United States Patent
Nakayama et al.

[11] Patent Number: 5,720,054
[45] Date of Patent: Feb. 24, 1998

[54] METHOD AND APPARATUS FOR SAMPLING URINE

[75] Inventors: Chiaki Nakayama; Kuniaki Shinohara; Takanori Matsuno; Toshio Koguro; Hiroshi Tsuboi; Naoki Sato, all of Kita-kyushu, Japan

[73] Assignee: Toto Ltd., Fukuoka, Japan

[21] Appl. No.: 513,770

[22] PCT Filed: Dec. 27, 1994

[86] PCT No.: PCT/JP94/02265

§ 371 Date: Mar. 5, 1996

§ 102(e) Date: Mar. 5, 1996

[87] PCT Pub. No.: WO95/18374

PCT Pub. Date: Jul. 6, 1994

[30] Foreign Application Priority Data

Dec. 30, 1993 [JP] Japan ................... 5-354284
Feb. 23, 1994 [JP] Japan ................... 6-051283
Feb. 23, 1994 [JP] Japan ................... 6-051285
Feb. 23, 1994 [JP] Japan ................... 6-051286
Feb. 23, 1994 [JP] Japan ................... 6-051287

[51] Int. Cl.$^6$ .................................................. E03D 11/00
[52] U.S. Cl. ........................................... 4/420; 4/661
[58] Field of Search ........................... 4/314, 661, 420, 4/300, 144.1; 128/760, 771

[56] References Cited

U.S. PATENT DOCUMENTS

| | | |
|---|---|---|
| 4,636,474 | 1/1987 | Ogura et al. |
| 4,961,431 | 10/1990 | Ikenaga et al. |
| 4,962,550 | 10/1990 | Ikenaga et al. |
| 4,982,741 | 1/1991 | Saito et al. |
| 5,073,500 | 12/1991 | Saito et al. |
| 5,111,539 | 5/1992 | Hiruta et al. |
| 5,184,359 | 2/1993 | Tsukamura et al. |
| 5,625,911 | 5/1997 | Nakayama et al. ............ 4/661 |

FOREIGN PATENT DOCUMENTS

| | | |
|---|---|---|
| 59-217844 | 12/1984 | Japan. |
| 60-117155 | 6/1985 | Japan. |
| 60-233551 | 11/1985 | Japan. |
| 62-187253 | 8/1987 | Japan. |
| 63-6291 | 2/1988 | Japan. |
| 1-136573 | 9/1989 | Japan. |
| 3-139334 | 6/1991 | Japan. |
| 5-19341 | 4/1993 | Japan. |
| 5-30764 | 4/1993 | Japan. |
| 6-230006 | 8/1994 | Japan. |
| 6-258315 | 9/1994 | Japan. |
| 6-258316 | 9/1994 | Japan. |
| 7-35745 | 2/1995 | Japan. |

*Primary Examiner*—Charles E. Phillips
*Attorney, Agent, or Firm*—Finnegan, Henderson, Farabow, Garrett & Dunner, L.L.P.

[57] ABSTRACT

A method and an apparatus (26) for sampling urine at a toilet equipped with a standard water closet bowl fixture. An elongated urine sampling vessel (96) extending transversely of the bowl fixture is used. While supported in such a manner that the axis thereof extends horizontally and perpendicular to the vertical central plane of the bowl fixture, the urine sampling vessel (96) is moved along the inner surface of the bowl (16) of the fixture and is brought to an optimum sampling position in the bowl space (16A). As the urine sampling vessel is adapted to any fore-and aft and lateral deviation of the direction of urination of an individual, urine is effectively sampled even by a sampling vessel which is small in size. The sampling vessel (96) is mounted to an end of a swing arm (94) having a horizontal pivot axis. In a simplest form of embodiment, only rotational movement is imparted to the swing arm (94). In a more sophisticated embodiment, the sampling vessel is brought to the sampling position by the rotational and translational movements of the swing arm. After use, the sampling vessel is stored in a washing chamber (162) substantially concealed by the frontal part of a toilet seat (24) and is washed by water under pressure ejected from a spray nozzle (184). In a preferred embodiment, a urine sampling apparatus (26) is mounted to the toilet seat.

49 Claims, 25 Drawing Sheets

METHOD AND APPARATUS FOR SAMPLING URINE

TECHNICAL FIELD

The present invention relates to a method and an apparatus for in situ sampling urine excreted by the individuals at a toilet installed in residences, offices or other facilities to obtain urine sample for use in urine analysis. More specifically, the present invention relates to a method and an apparatus capable of sampling urine at a toilet equipped with a standardized water closet bowl fixture commercially available on the market.

BACKGROUND ART

In view of the trends for longevity of the individuals, the importance of health care and maintenance has been receiving increasing attention. As urine is an important source of information that represents the health conditions of an individual, various dysfunction such as pancreatic disorders (typically, diabetes), hypohepatia, and kidney disorders can be detected advantageously in a non-invasive manner by performing quantitative analysis of certain urine constituents, such as glucose, protein, urobilinogen, occult blood and other substances. Accordingly, proposed in the art are toilets having a urinalysis function which are capable of performing sampling and analysis of urine so as to assist the individuals in rendering their health check by making use of toilets provided in residences, offices and other facilities.

For instance, JP-A-59-217844 of Toto Ltd., U.S. Pat. No. 4,961,431 to Ikenaga et al., U.S. Pat. No. 4,962,550 to Ikenaga et al., U.S. Pat. No. 4,982,741 to Saito et al., U.S. Pat. No. 5,073,500 to Saito et al., U.S. Pat. No. 5,111,539 to Hiruta et al., and U.S. Pat. No. 5,184,359 to Tsutamura et al., propose to form a urine sampling cavity or sampling well on the bowl surface of a water closet bowl fixture to sample a quantity of urine excreted into the toilet bowl, the urine sample being subjected to urinalysis by way of liquid chromatographic process, colorimetric analysis process, or polarographic or voltammetric process.

The advantage of these sampling systems which are designed to make use of the urine sampling cavity or sampling well formed on the bowl surface is that urine excreted into the toilet bowl is received and collected by a considerably wide surface area of the bowl so that urine is readily sampled regardless of the direction of urination or the variation in the trajectory of urine column. Therefore, an adequate quantity of urine necessary for urinalysis can easily be sampled even in the case of elderly people who are apt to suffer from the shortage of the amount of urine per urination.

However, the problem associated with these systems is that they require a special-purpose toilet bowl fixture provided with a urine sampling cavity or well formed on the bowl surface for the purposes of sampling of urine so that a standard-type toilet bowl fixture having the conventional bowl configuration cannot be used. Accordingly, in order to sample urine and perform urinalysis at a toilet of residence, office or other facility, the existing conventional bowl fixture must first be removed and then a special purpose bowl fixture envisioned for sampling and urinalysis must be installed. This involves a great deal of labor and expenses for reform works and necessitates to discard the existing bowl fixture.

Furthermore, as such special purpose toilet bowl fixtures must be manufactured specially and separately from standard-type toilet bowls, it is difficult to produce them via the mass production process. As a result, these systems are too expensive to be installed widely in regular households and offices.

Another disadvantage is the difficulty in obtaining a good urine specimen since residual flushing water remaining in the urine sampling cavity of the bowl surface after flushing of the bowl tends to dilute the fresh urine to be sampled. Similarly, the fresh urine sample is susceptible to contamination by residual urine and feces since the urine sampling section is formed on the bowl surface.

In FIG. 4 of JP-A-62-187253 of K.K. Inax, there is disclosed a sampling apparatus wherein a swing arm supporting an excrement sampling vessel is rotated along the bowl surface of a toilet bowl fixture to sample urine or other excrement. The bowl is provided at the rear part thereof with a cavity serving as a testing region, the excrement sampling vessel being moved after sampling into the testing region wherein excrement is subjected to analysis. After use, the sampling vessel is washed in the same rear region. This apparatus also requires a special purpose bowl fixture provided at the rear part with the testing region and also suffers from the disadvantage that a standard toilet bowl fixture cannot be used.

JP-A-3-139334 of Matsushita Denko K.K. discloses a urine sampling and analyzing apparatus having a wheeled main body which is intended to be pulled aside of the toilet bowl fixture when in use and to be moved away into a non-obstructive location such as the corner of the toilet room when not in use. The main body supports a urine sampling cup in a telescoping fashion so that, when urine is to be sampled, the urine sampling cup is moved into the bowl through a gap defined between the toilet bowl and the toilet seat. A testing strip is dipped into the urine sample sampled by the sampling cup and is tested for urinalysis.

The advantage of this apparatus is that urine can be sampled by using a standard-type toilet bowl fixture.

However, the problem involved in this apparatus is that the wheeled main body as placed on the toilet floor occupies the toilet floor and therefore hinders cleaning of the toilet as well as routine use of the toilet for the purposes of excretion. Handling and manipulation of the apparatus is cumbersome because, each time the apparatus is used, the main body must be moved toward and away from the toilet bowl in order to position the apparatus in a non-obstructive location after use.

Furthermore, the position of the sampling cup is so high that the cup interferes with or comes too close to the body of the user as seated on the toilet seat because the sampling cup is inserted through the gap between the bowl and the toilet seat in the lateral direction to extend above the bowl. Moreover, the user must control the position of the main body of the apparatus by the hands to ensure that the sampling cup is properly positioned to meet the trajectory of falling urine. As a result, sampling of urine is extremely difficult to perform so that there is a risk of failure of sampling.

U.S. Pat. No. 4,636,474 to Ogura et al., JP-A-60-117155 of Toshiba K.K., and JP-U-1-136573 of Matsushita Denko K.K. disclose urinalysis apparatus wherein a swingable arm is mounted for pivoting movement to a toilet seat, with a urine sensor being arranged at the free end of the arm to analyze urine upon contact with urine excreted into the bowl. Similarly, JP-A-60-233551 of Matsushita Denki Sangyo K.K. discloses a urinalysis device which comprises a casing adapted to be hanged on the rim of the bowl fixture, an arm extending from the casing into the bowl, a spoonshaped urine sampling vessel mounted to the end of the arm, and a urine sensor arranged in the sampling vessel. These apparatus also enjoy the advantage that they can be used in combination with the standard toilet bowl fixtures.

However, contacting the sensor directly with the original urine gives rise to several problems. Thus, in contrast to diagnosis by way of blood wherein the hydrogen ion concentration (pH), the chlorine ion concentration and the oxygen concentration are constantly conditioned to a high degree by various physiological organs, urine as an excrement from the human body is subject to a wide range of variations in the pH, the chlorine ion concentration and the oxygen concentration from sample to sample so that it is difficult to perform a high degree of analysis for a particular urinal constituent unless urine as sampled is diluted by a buffer. In addition, contacting the sensor directly with the original urine without dilution causes premature degradation of the sensor and reduces the service life thereof. Further, it is impossible to perform urinalysis for a plurality of items because it is difficult to arrange a plurality of sensors at the end of the swingable arm.

JP-U-5-30764 of NOK K.K. proposes a health diagnostic apparatus which is adapted to sample a quantity of urine by a urine sampling mechanism attached to a toilet seat and to transfer it to an analyzer station for urinalysis. In order to sample urine excreted from the user seated on the toilet seat by receiving it in mid air within the toilet bowl, a swingable arm is pivoted at an end thereof to the underside of the toilet seat for swinging movement about a vertical axis, the other end of the arm being provided with a vertically elongated urine sampling cup. There is described that the arm may be rotated manually or electrically. Urine sampled by the sampling cup is drawn by a manual or automatic syringe and, after being mixed with liquid reagent, is forwarded to the measuring station including an absorption spectrophotometer in which it is subjected to analysis.

This health diagnostic apparatus also enjoys the advantage of sampling urine by making use of an existing or standard toilet bowl fixture without requiring a specially-fabricated toilet bowl fixture, since urine is sampled in mid air by the sampling cup which is moved within the inner space of the bowl. Furthermore, a high degree of analysis can be achieved as urine specimen is subjected to analysis after being diluted by the liquid reagent.

However, the problem of this apparatus is that it is difficult to realize a commercially feasible form of the urine sampling mechanism. For the urine sampling mechanism to be commercially feasible, several performances must be fulfilled.

More specifically, the direction of urination is subject to fluctuation depending on the difference in the sexuality of the user to the extent that in the case of a male the urine column tends to fall relatively forwardly in contrast to a female whose urine column tends to fall rearwardly. In addition, the direction of urination varies from individual to individual so that the direction deviates each time depending on the posture of the user as seated on the toilet seat. As a result, the trajectory of the urine column tends to deflect in the fore-and-aft direction as well as in the lateral direction. However, it is desirable that a urine sampling mechanism be capable of reliably and readily sampling urine regardless of any fluctuation in the trajectory of urine column that would result due to the sexual difference of the user or due to the variation in the posture of the user as seated on the toilet seat. This is particularly important when the total quantity of urine per urination is limited as is the case of elderly people who have increasing needs for urinalysis.

In order to sample urine without failure despite the occurrence of such a fluctuation in the trajectory of urine column, it would be desirable that the sampling vessel be made as large in size as possible. Otherwise, the chance of sampling would be lost if the urine column unfortunately fails to hit right on the sampling vessel. On the other hand, however, it is also desirable that, when not in use, the sampling vessel be readily stored in a non-obstructive place situated, for example, underneath the toilet seat, because the toilet must also be used for the purposes of routine excretion insofar as the urine sampling is performed by making use of a standard toilet fixture. To this end, therefore, another requirement imposed on the design of the urine sampling vessel is that it must be made sufficiently small in size and must be designed in such a form that facilitates storage. The urine sampling mechanism proposed in JP-U-5-30764 is difficult to meet with these opposing requirements because a cylindrical sampling cup elongated in the vertical direction is adopted.

Furthermore, with the urine sampling mechanism disclosed in JP-U-5-30764, it is impossible to move the sampling cup along the central plane of the bowl fixture since the urine sampling cup is displaced along an arcuate path around a vertical pivot axis. If the sampling cup is rotated so as to follow the deviation of the fall position of urine column in the fore-and-aft direction, the position of the sampling cup will undesirably be shifted in the lateral direction. As a result, it is difficult to sample excreted urine effectively and without failure.

It is also desirable that sampling of urine may be carried out with an easy posture. In this regard, it will be noted that a part of the buttocks will slightly sag beyond the seat due to body weight as the user is seated on the toilet seat. Since in the diagnostic apparatus cited above, the swing arm is mounted to the toilet seat and is adapted to rotate about a vertical pivot axis, the path of the sampling cup as it is rotated is so high that the sampling cup interferes with the buttocks of the user or, in the case of male, the penis. Practically, therefore, it would be difficult for the user to avoid interference with the sampling cup unless the user urinates while lifting the buttocks away from the toilet seat.

It is further desirable that the urine sampling vessel soiled by urine be thoroughly washed and cleansed after use. Otherwise, residual urine of previous urination would contaminate fresh urine sample during subsequent sampling thereby precluding to obtain a good urine specimen necessary to perform a high degree of urinalysis. Furthermore, the sampling vessel soiled by residual urine gives rise to bad odor and unhygienic feeling.

It is considered that the urine sampling mechanism of JP-U-5-30764 is not suitable to meet with these requirements and, for this reason, is not commercialized as yet.

It is also desirable that the urine sampling mechanism be readily mounted to a toilet seat without impairing the mechanical strength and sealability of the seat. In this regard, however, severe designing requirements are imposed when a urine sampling mechanism is to be installed to a toilet seat. Thus, in the conventional toilet, only a limited gap as small as about 1.5–2 cm is available between the lower surface of the toilet seat and the upper surface of the rim of the toilet bowl. The radial space available within the bowl to arrange the urine sampling mechanism is also limited. As a result, in order to install a urine sampling mechanism by utilizing such extremely narrow limited gap and space, severe dimensional restrictions and restraints are imposed on the design of the urine sampling mechanism. If the urine sampling mechanism were designed small enough to be readily accommodated within such a narrow gap, the urine sampling mechanism would become quite refined and delicate so that the durability of the movable parts thereof and the reliability of operation would be decreased. In addition, as the urine sampling cup is made smaller, the aperture thereof for receiving urine would be reduced which, in turn, decreases the probability of urine sampling. Accordingly, the probability of sampling must be sacrificed if the urine sampling mechanism is to be made small and compact.

If, to the contrary, the urine sampling mechanism is to be made larger, then an existing toilet seat must be subjected to substantial processing and machining works, such as by cutting away a part thereof, in order to install the mechanism in a swingable manner within the narrow space defined between the lower surface of the toilet seat and the upper surface of the rim of the toilet bowl. In that event, installation of the urine sampling mechanism would be complicated and difficult to perform thereby increasing the amount of work and expense involved. In addition, by tampering with the toilet seat, the reliability of the operation of the urine sampling mechanism is reduced and the mechanical strength of the seat is impaired.

Accordingly, the primary object of the present invention is to provide a method and an apparatus for sampling urine at a toilet equipped with a conventional standard water closet bowl fixture, which are capable of sampling urine readily and without failure regardless of a fluctuation in the trajectory of urine column that would occur in the fore-and-aft direction or in the lateral direction due to the sexual difference of the user or due to the variation in the posture of the user as seated on the toilet seat.

Another object of the invention is to provide a method and an apparatus for sampling urine which are capable of effectively sampling urine while making use of a urine sampling vessel designed in such a form as to facilitate storage thereof when not in use.

A still another object of the invention is to provide a method and an apparatus for sampling urine which are capable of sampling urine without failure even when the user urinates with an easy posture.

A further object of the invention is to provide a method and an apparatus for sampling urine which do not hinder cleaning and routine use of the toilet.

Another object of the invention is to provide a urine sampling apparatus which is commercially feasible.

Another object of the invention is to provide a urine sampling apparatus equipped with a cleansing device which is operable to wash the urine sampling vessel after use to keep it clean and which is small and compact in size.

Commercially available standard toilet bowl fixtures have a variety of bowl surface configuration that varies from model to model so that some models are provided with a raised bowl surface configuration whereas other models have a deeply depressed bowl surface configuration. If the path or locus of the urine sampling vessel were designed and determined in conformity with those toilet bowl fixtures having a deeply depressed bowl surface configuration in such a manner that the urine sampling vessel is rotated along the bowl surface down to the bottom central region of the bowl, the sampling vessel would interfere with the bowl surface of the other bowl fixtures having a raised bowl surface configuration. Accordingly, another object of the invention is to provide a urine sampling apparatus which is able to readily adjust the path of the sampling vessel in conformity with various bowl surface configuration of commercially available standard toilet bowl fixtures.

DISCLOSURE OF THE INVENTION

The present invention provides a method and an apparatus for sampling urine excreted by an individual seated on a toilet seat at a toilet equipped with a standard water closet bowl fixture. The feature of the urine sampling method and apparatus according to the invention resides in the use of an elongated urine sampling vessel that extends in a substantially horizontal fashion. While holding the urine sampling vessel in such a manner that the axis thereof extends substantially horizontally and substantially perpendicular to the vertical central plane of the toilet bowl fixture, the urine sampling vessel is moved along the inner surface of the bowl and is brought to a urine sampling position located within the inner space of the bowl thereby to sample urine excreted into the bowl. Preferably, the urine sampling vessel is moved such that the longitudinal center of the urine sampling vessel is situated in the vertical central plane of the bowl fixture. After use, the urine sampling vessel is stored in a storage position substantially concealed by the frontal part of the toilet seat and is washed with water under pressure ejected from a spray nozzle.

As in this manner a transversely-extending elongated sampling vessel is used and because the sampling vessel is held in such a manner that the longitudinal axis thereof extends perpendicular to the vertical central plane of the bowl fixture, the sampling vessel will lie for a predetermined length thereof in a substantially transverse direction with respect to the direction of urination of the user. As a result, even though the direction of urination is deviated laterally to some degree from the vertical central plane of the bowl fixture, the urine column will fall within the coverage of the transverse length of the sampling vessel whereby urine is effectively sampled.

With respect to any deviation of urine column that would occur in the fore-and-aft direction of the bowl fixture, the sampling vessel may promptly be brought to an optimum sampling position by swinging the sampling vessel in the fore-and-aft direction. Accordingly, in the event that the direction of urination is deviated in the fore-and-aft direction due to the difference in sexuality or physical features of the user, the sampling vessel may readily be adjusted to compensate for any such deviation. It is preferable that urine sampling for a male is carried out with the sampling vessel positioned at a sampling position situated adjacent the inclined frontal wall of the bowl and that urine sampling for a female is carried out with the sampling vessel positioned at a sampling position situated adjacent the bottom region of the bowl between the inclined frontal wall of the bowl and a discharge well.

Since the urine sampling vessel is adapted in this way in the lateral direction as well as in the fore-and-aft direction so as to cover any deviation of urine column in consideration of the tendencies of urination that are exhibited at a toilet by different individuals, it is possible to sample urine without failure while using a sampling vessel which is small in size. Consequently, urine may readily be sampled by making use of a standard toilet bowl fixture, without recourse to a special-purpose toilet bowl fixture wherein a sampling cavity is formed on the bowl surface for a wide surface area. Because the sampling vessel is transversely elongated, the sampling vessel when not in use may readily be stored in a narrow space defined between the frontal part of the toilet seat and the upper surface of the bowl or in a storage chamber located inwardly of the frontal part of the rim of the bowl fixture.

The elongated sampling vessel is moved between a rest or storage position and a sampling position by a swing arm and a drive mechanism therefor, the sampling vessel being preferably detachably mounted to the free end of the swing arm.

In a simplest form of the urine sampling apparatus according to the invention, the swing arm is pivotally supported by a frame supported by the standard toilet bowl fixture and is rotated preferably by an electric drive including an electric motor. The frame may be mounted to the toilet seat, to a housing mounted to the bowl fixture, or to the rim of the toilet bowl. As the sampling vessel is displaced along the inner surface of the bowl, the sampling vessel does not interfere with the body of the user seated on the toilet seat. Accordingly, the sampling apparatus of the invention is comfortable to use and any inadvertent damage that my occur on the movable parts of the electrical drive due to contact with the user's body is avoided.

In a more sophisticated form of the urine sampling apparatus of the invention, the electric drive is designed to impart to the swing arm a rotational movement about a horizontal axis as well as a translational movement in the fore-and-aft direction in such a manner that the sampling vessel is moved along any desired path. In this form, the sampling vessel when not in use may be stored in a narrow space located between the frontal part of the rim of the bowl and the toilet seat. For sampling of urine released from a male user, the sampling vessel may be placed in position by displacing the sampling vessel horizontally and rearwardly away from the storage position and by rotating it along the inclined surface of the frontal part of the bowl. In the case of a female user, the sampling vessel may be positioned by displacing the sampling vessel further horizontally and rearwardly along the bottom surface of the bowl by way of a translational movement.

As the sampling vessel is thus moved in combination by the rotational movement and the translational movement, it is possible to precisely adapt the sampling vessel to any deviation of urine column taking place in the fore-and-aft direction. Such movements also permit to store the sampling vessel after use in a narrow space defined between the frontal part of the rim of the bowl and the toilet seat.

Preferably, the drive mechanism for the swing arm includes a slider and a lever and cam mechanism. With this arrangement, the path or locus of the sampling vessel may be altered by simply modifying the cam profile so that the path of the sampling vessel can readily be adapted in such a manner as to conform with various different bowl surface configurations of the commercially available standard toilet bowl fixtures.

The slider is preferably translated by a pinion and rack mechanism driven by a motor. With this arrangement, a single motor may be used to impart the rotational movement as well as the translational movement to the sampling vessel so that the urine sampling apparatus is made compact.

In the embodiment wherein the frame of the urine sampling apparatus is mounted to the toilet seat, the toilet seat is preferably provided at the lower surface thereof with a downwardly directed concavity in which at least a part of the electrical drive is accommodated. This arrangement enables to increase the size of the electrical drive so that a urine sampling apparatus which is robust and which has an improved operational reliability is realized. In addition, the urine sampling apparatus may be mounted to the toilet seat without impairing the mechanical strength and the sealability of the toilet seat.

Also, in the embodiment wherein the frame of the urine sampling apparatus is mounted to the toilet seat, the frame is preferably curved to extend along the toilet seat in such a manner that it is substantially concealed by the toilet seat in the horizontal position of the toilet seat. It is preferable that the frame is confined within a vertical gap defined between the upper surface of the rim of the bowl and the lower surface of the toilet seat. With this arrangement, the toilet seat as incorporating the urine sampling apparatus presents an improved appearance. Furthermore, a robust yet compact urine sampling apparatus can be realized while retaining the mechanical strength of the toilet seat.

In a preferred embodiment, the urine sampling vessel has a generally flat configuration and is provided with a rectangular inlet opening which extends transversely of the toilet bowl fixture in a direction substantially perpendicular to the radius of the swing arm. The sampling vessel has a urine pool or sump arranged at the rear part thereof, the front wall of the vessel being preferably inclined toward the urine pool. With this arrangement, the urine sampling vessel when held in a horizontal position provides a maximum content and effectively receives urine excreted into the bowl. When held in a vertical position, the fore-and-aft dimension of the sampling vessel is shortened so that it is readily stored in a narrow washing chamber.

These features and advantages of the invention, as well as other features and advantages thereof, will become apparent from the following description made with reference to the preferred embodiments thereof.

BEST MODE FOR CARRYING OUT THE INVENTION

The urine sampling method and apparatus according to the invention will be described in more detail with reference to the accompanying drawings. The first embodiment of the urine sampling apparatus according to the invention wherein the urine sampling apparatus is mounted to the toilet seat will first be described with reference to FIGS. 1–20.

Figure 1:
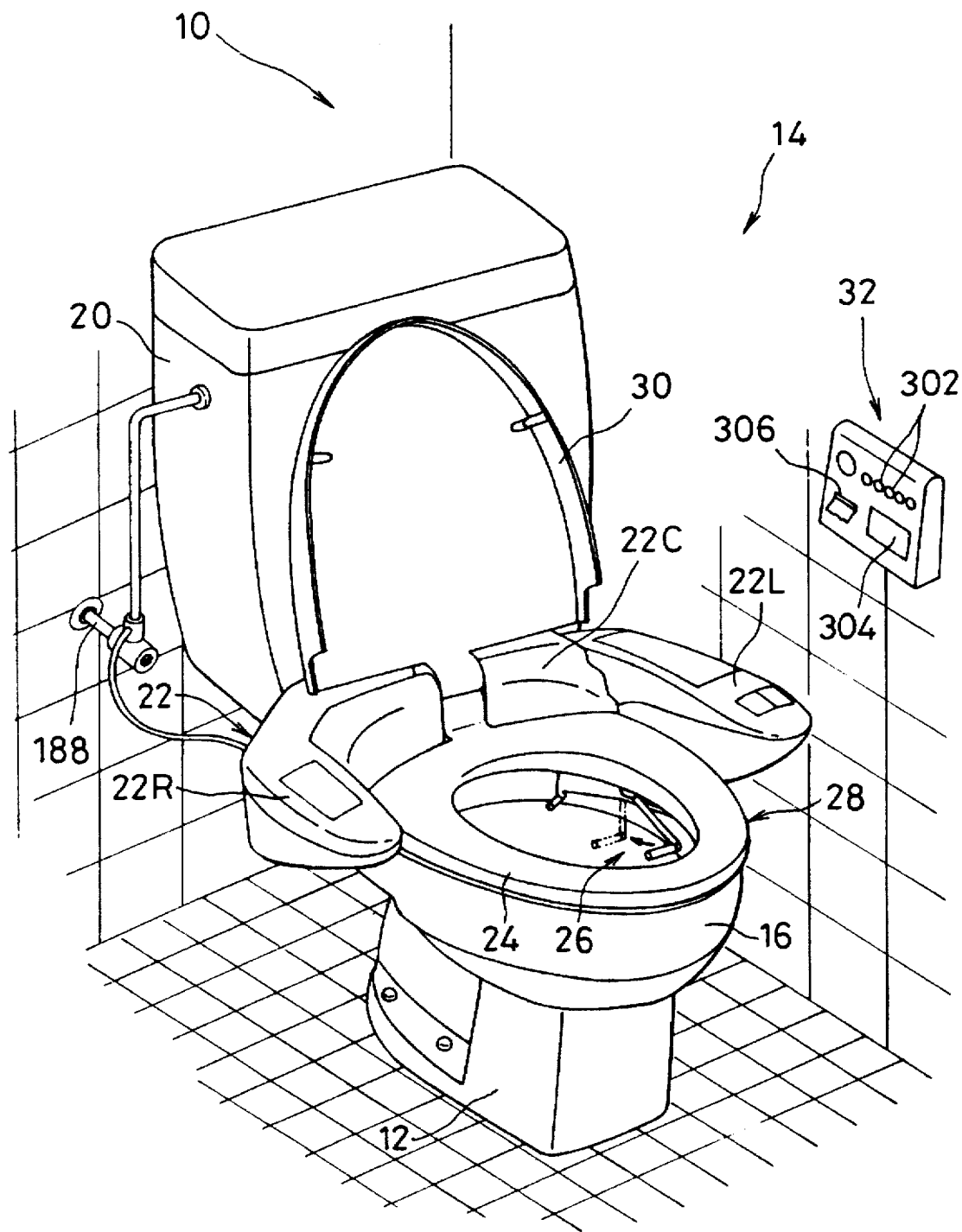
FIG. 1 is a perspective view showing a urinalysis unit provided with a urine sampling apparatus according to the first embodiment of the invention as mounted to a standard water closet bowl fixture of a toilet.
Figure 2:
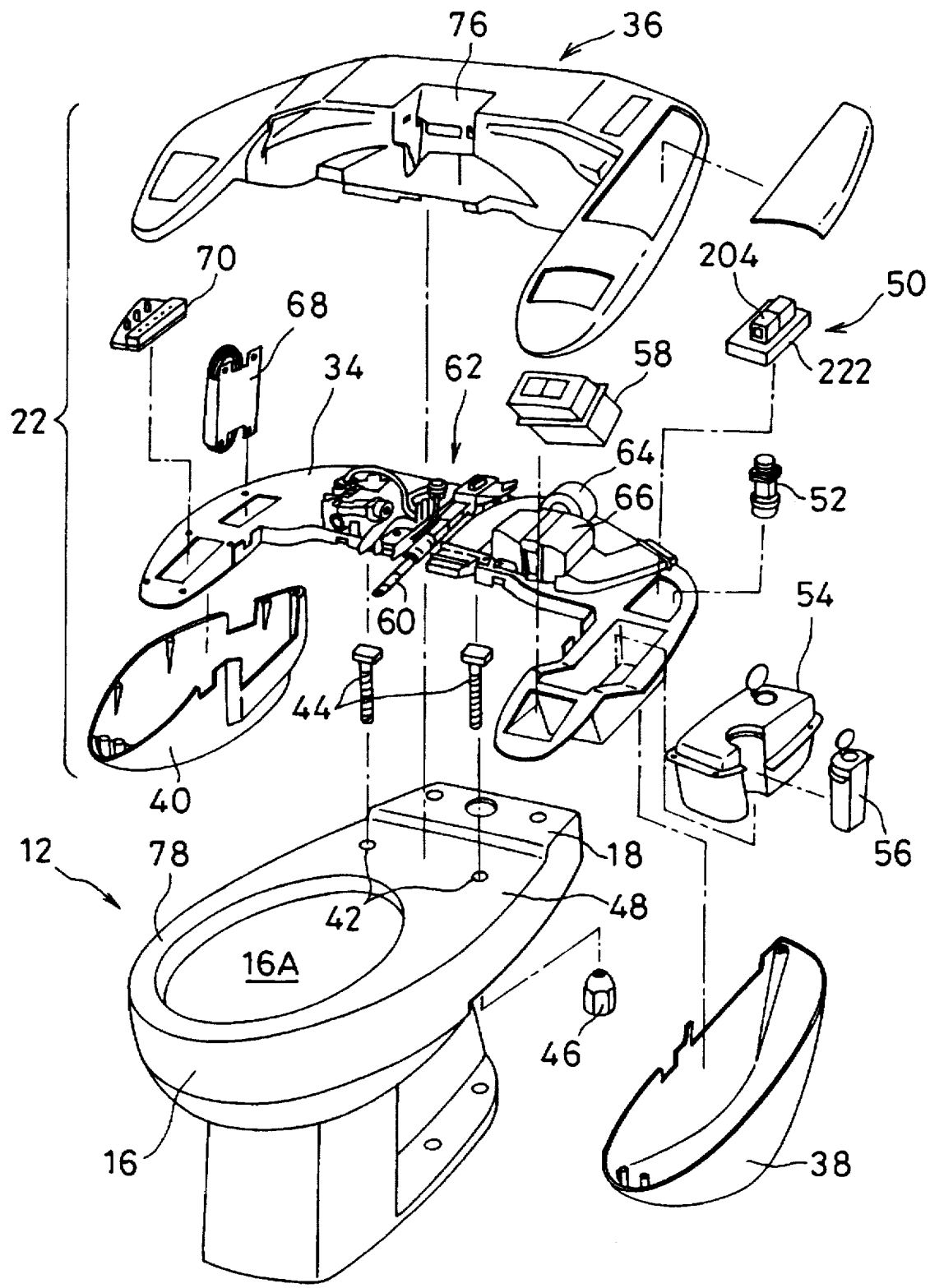
FIG. 2 is an exploded perspective view of a housing of the urinalysis unit illustrated in FIG. 1.
Figure 3:
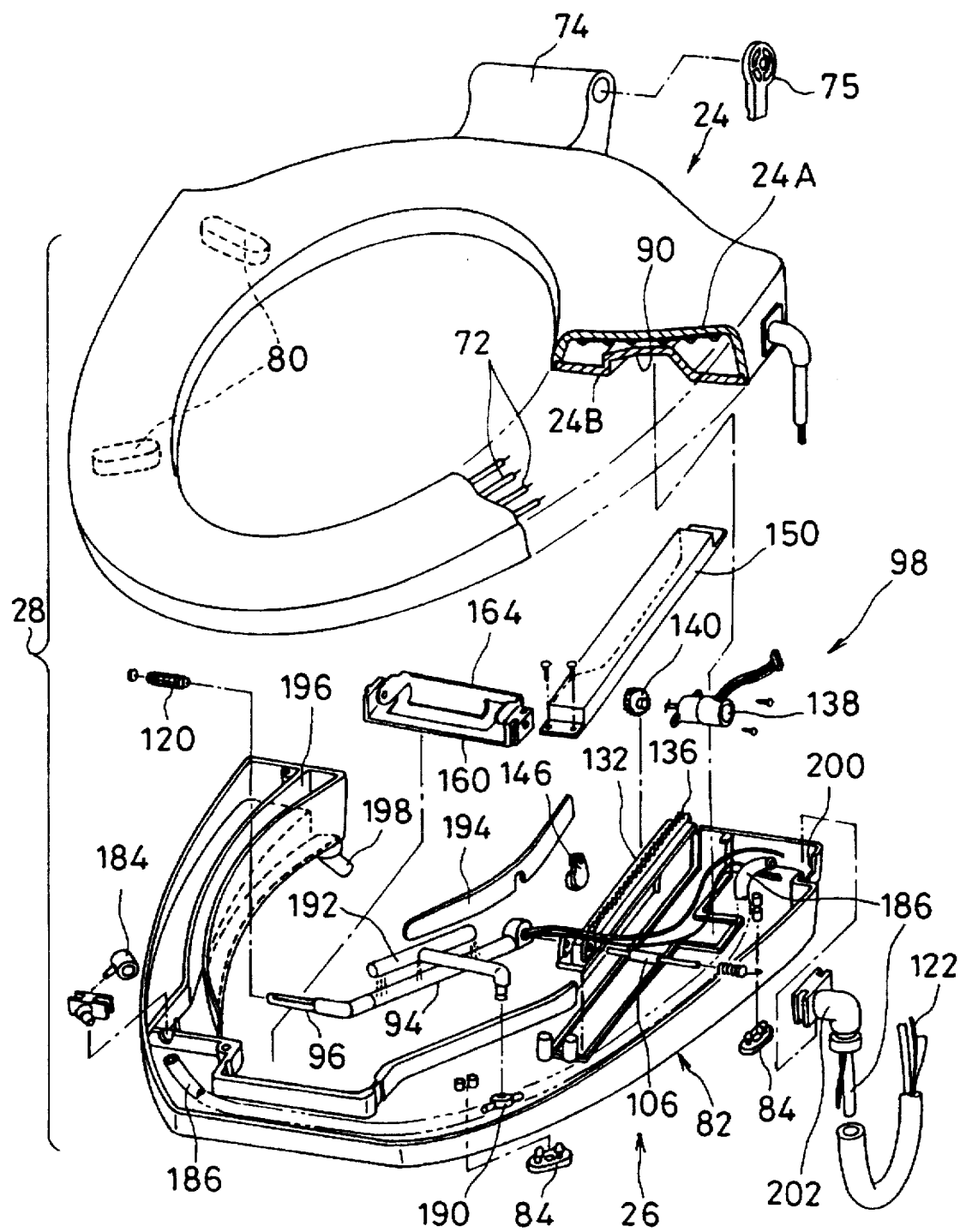
FIG. 3 is an exploded perspective view, partly cut away, of a toilet seat assembly shown in FIG. 1 and wherein the urine sampling apparatus is incorporated.

Referring to FIGS. 1–3, the toilet 10 is provided with a standard water closet bowl fixture 12 which is installed on the toilet floor in the conventional manner. A urinalysis unit 14 provided with the urine sampling apparatus according to the invention is mounted to the toilet bowl fixture 12 to sample urine of an individual at the toilet and to subject it to urinalysis. The urinalysis unit 14 may be mounted to any standardized toilet bowl fixture available on the market, including vortex type, siphon type, siphon jet type, and wash-down type. The standard bowl fixture is provided with a conventional bowl 16 and a flushing water supply section 18 located rearwardly of the bowl. In the illustrated embodiment, the flushing water supply section comprises a cistern mounting section 18 to which a conventional cistern 20 is mounted in a conventional manner. The urine sampling method and apparatus according to the invention may equally be applicable to a toilet having a toilet bowl fixture of the type in which flushing water is supplied through a flushing pipe equipped with a flushing valve instead of a cistern.

The toilet includes a housing 22 which is fixed to the bowl fixture 12 as described later and a toilet seat 24 which is pivotally hinged to the housing 22. In the first embodiment illustrated, the toilet seat 24 is provided with a urine sampling apparatus 26 according to the invention which is adapted to sample urine in mid air within the inner space 16A of the bowl, the toilet seat 24 and the sampling apparatus 26 forming together a built-in toilet seat assembly 28 (referred-to hereinafter as "toilet seat assembly"). The toilet seat assembly 28 is preferably prefabricated by assembling the urine sampling apparatus 26 to a specially made toilet seat 24. A conventional toilet lid 30 may also be hinged to the housing. A control unit 32 for controlling the urinalysis unit 14 and for outputting the results of urinalysis may be disposed on the side wall of the toilet.

As shown in FIG. 2, the housing 22 of the urinalysis unit 14 may comprise, for example, a frame 34, an upper casing 36 and a pair of lower casings 38 and 40. These component parts of the housing 22 may be formed by injection molding of plastics and may be fastened together by screws and the like to form an integral housing 22. As shown in FIG. 2, the conventional standard toilet bowl fixture 12 is generally provided, between the bowl 16 and the flushing water supply section 18, with a pair of seat mounting holes 42 for use in mounting the conventional toilet seat. The housing 22 of the urinalysis unit 14 is also secured to the bowl fixture 12 by making use of these holes 42. To this end, the frame 34 of the housing 22 is fixed on the upper surface 48 of the bowl fixture 12 between the bowl 16 and the cistern mounting section 18 by engaging a pair of T-bolts 44 into a pair of T-shaped slots formed on the underside of the frame 34 as described in JP-Y-63-6291 and by inserting the T-bolts 44 through the seat mounting holes 42 followed by screwing associated nuts 46.

As best shown in FIG. 2, the frame 34 has a central portion extending transversely of the bowl fixture 12 and a pair of lateral portions extending forwardly from the ends of the central portion, the upper casing 36 being shaped to conform to the frame 34. Accordingly, the frame 34, the upper casing 36 and the lower casings 38 and 40 concert together to form the central portion 22C, left-hand lateral portion 22L and the right-hand lateral portion 22R of the housing 22 as shown in FIG. 1.

As shown in FIG. 2, within the left lateral portion 22L of the housing, there may be arranged a urinalysis device 50 for analyzing the urine sample sampled by the urine sampling apparatus 26, an electrically driven syringe pump 52 for transferring urine sample and carrier liquid to the urinalysis device 50, a carrier liquid reservoir 54, and a reservoir 56 for calibration solution. The urinalysis device 50 may include a flow cell suitable for polarographic or colorimetric analysis. A digital sphygmomanometer unit 58 may additionally be arranged on the left-hand portion 22L of the housing to enable the user to monitor the artery blood pressure by engaging the left second finger of the user. The digital sphygmomanometer unit 58 need not be described as it does not form part of the invention. In the illustrated embodiment, a conventional bidet system 62 having a spray nozzle 60 for producing an upwardly directed spray to wash the perineal part of the user, a conventional hot-air blower and drier unit 64, and a conventional deodorizer unit 66 with an ozonizer are arranged within the central portion 22C to provide additional functions when the toilet 10 with the urinalysis unit 14 is used for routine purposes. However, these additional functions are not indispensable for the purpose of the present invention and may therefore be omitted. A power source 68 for the urinalysis unit 14 and a control panel 70 for the bidet system may be stored within the right lateral portion 22R of the housing.

Referring primarily to FIGS. 3–9, the toilet seat assembly 28 comprised of the toilet seat 24 and the urine sampling apparatus 26 incorporated the rein will be described. In the illustrated embodiment, the toilet seat 24 is designed and manufactured in an attempt to incorporate the urine sampling apparatus 26 the rein and, accordingly, has a design suitable to meet with this purpose. As shown cut away in FIG. 3, the toilet seat 24 may be formed from an upper half 24A and a lower half 24B of impact resistive plastics which are joined together by high-frequency fusion bonding, with an electric heater wire 72 for heating the toilet seat being arranged as required. The seat 24 may be pivotally mounted to the housing 22 by a suitable hinge. Preferably, the seat 24 is mounted to the housing 22 by journaling the hinge portion 74 thereof by a retainer block 75 as described in Japanese Utility Model Application No. 5-19341 and by engaging the retainer block 75 within a bearing portion 76 (FIG. 2) of the housing 22.

In order to accommodate the toilet seat to any sintering distortion that may be developed in the bowl fixture 12 as a result of sintering process during the production thereof, the toilet seat 24 is preferably supported at four points against the upper surface of the rim 78 of the bowl fixture 12 in a manner similar to the conventional toilet seat. To this end, a pair of support legs 80 with cushioning pads may be provided in the conventional manner at the underside of the seat 24 as shown by dotted line in FIG. 3. At the other two points, the toilet seat 24 is supported by a pair of legs 84 mounted to a casing or frame 82, described later, of the urine sampling apparatus. As will be understood from FIGS. 6 and 9, due to the presence of the legs 80 or 84, an annular gap having a height of about 1.5–2 cm is left between the upper surface 86 of the rim 78 of the bowl fixture and the lower surface 88 of the seat 24. By making use of a part of the annular gap, the frame 82 of the urine sampling apparatus 26 is arranged and the urine sampling vessel of the sampling apparatus 26 is accommodated the rein as described later. Furthermore, as will be apparent from FIGS. 3, 6 and 9, the toilet seat 24 is provided at the underside thereof with a pair of downwardly directed concavities 90 and 92 so as to accommodate part of the components of the urine sampling apparatus 26 as described later.

In the first embodiment illustrated, the urine sampling apparatus 26 is generally designed such that a quantity of urine released into the bowl 16 of the bowl fixture 12 is received in mid air in the inner space 16A of the bowl by a urine sampling vessel and that after sampling the sampling vessel is returned to a storage position underneath the toilet seat and is automatically washed with water. Referring to FIGS. 3–9, in the embodiment shown, the urine sampling apparatus 26 includes a generally crank-shaped swing arm 94, an elongated urine sampling vessel 96 detachably mounted to the free end of the swing arm, an electrical drive 98 for supporting and driving the swing arm 94, and the frame 82 for the urine sampling section, the drive 98 being mounted to the frame 82. The swing arm 94 may be formed by a central elbow 100, an end elbow 102, a pipe 104 connecting these elbows, and a spindle 106, as shown in FIGS. 5 and 8.

Figure 7:
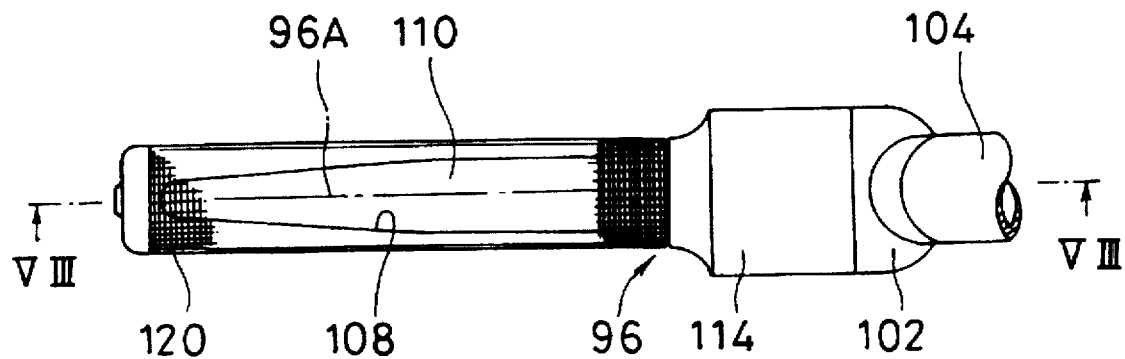
FIG. 7 is a top plan view of the urine sampling vessel mounted to the swing arm.
Figure 8:
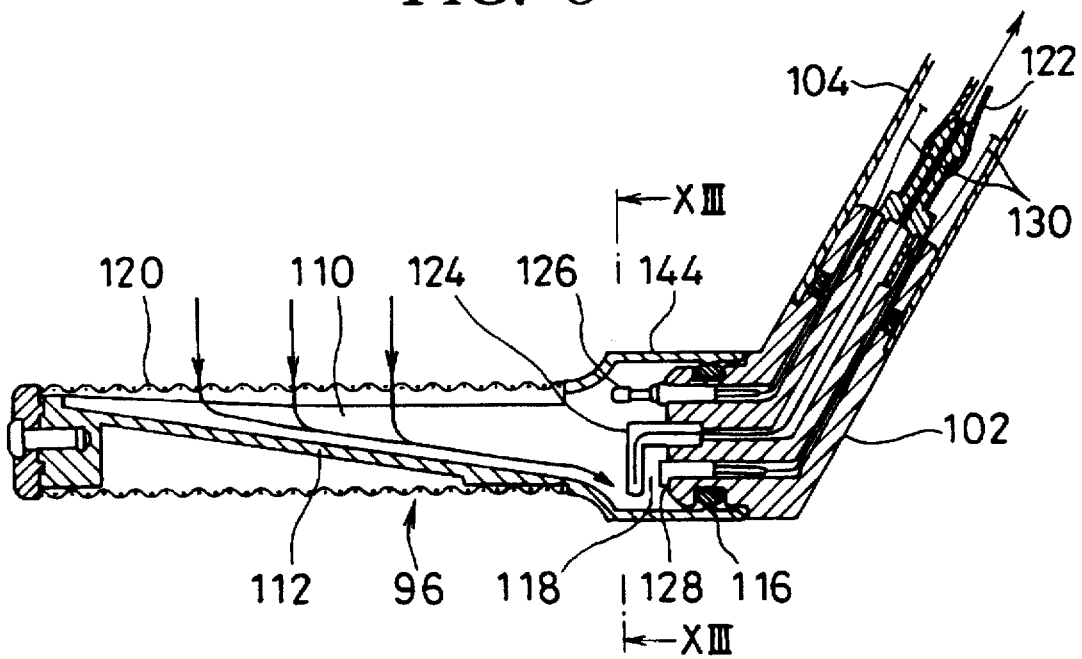
FIG. 8 is a cross-sectional view taken along the line VIII—VIII of FIG. 7.

As shown in FIGS. 7 and 8, in the illustrated embodiment, the urine sampling vessel 96 may be comprised of a main body 112 having an elongated upper opening 108 and a trough-shaped cavity 110 and of a base 114 having an enlarged diameter. The urine sampling vessel 96 is supported by the swing arm 94 in such a manner that the longitudinal axis 96A (FIG. 7) thereof extends perpendicular to the vertical central plane 12A (FIG. 4) of the bowl fixture. The urine sampling vessel 96 is detachably and liquid tightly mounted to the end elbow 102 by means of an O-ring 116 to permit the sampling vessel 96 to be removed from the swing arm 94 for cleaning and replacement.

The cavity 110 formed in the main body is inclined toward the base 114 to ensure that urine fallen down into the cavity 110 is accumulated within a urine pool or sump 118 defined by the base 114 and the elbow 102. Preferably, the outer periphery of the main body 112 is covered by a metal screen 120 to prevent urine excreted by the user and impinging on the urine sampling vessel 96 from splashing backwards and to effectively collect urine sample. Urine accumulated in the urine pool 118 is forwarded via a flexible tube 122 extending through an inner passage of the elbow 102 as well as through the swing arm 94 and its spindle 106 to the urinalysis device 50 located in the housing 22 under the action of the syringe pump 52 operating on its suction and delivery strokes.

In order to ensure that only such urine that is free from air bubbles is picked up for delivery to the urinalysis device so as to enhance the stability of analysis, it is desirable that urine be drawn from the bottom of the urine pool 118. To this end, the elbow 102 is provided with an L-shaped suction pipe 124 which is open toward the bottom of the urine pool 118. A pair of vertically spaced electrodes 126 and 128 may be provided on the elbow 102 to detect whether a sufficient amount of urine has accumulated within the urine pool 118. These electrodes may be connected via lead wires 130 to a control circuit of the urinalysis device 50 arranged in the lateral housing 22L to permit the control circuit to detect accumulation of urine in the urine pool 118 by monitoring the electric resistance of the gap between the electrodes 126 and 128. As the flexible tube 122 as well as the lead wires 130 are arranged to extend in part within the swing arm 94, the outer configuration of the swing arm 94 is simplified and any damage on the flexible tube 122 and the lead wires 130 is prevented.

Figure 9:
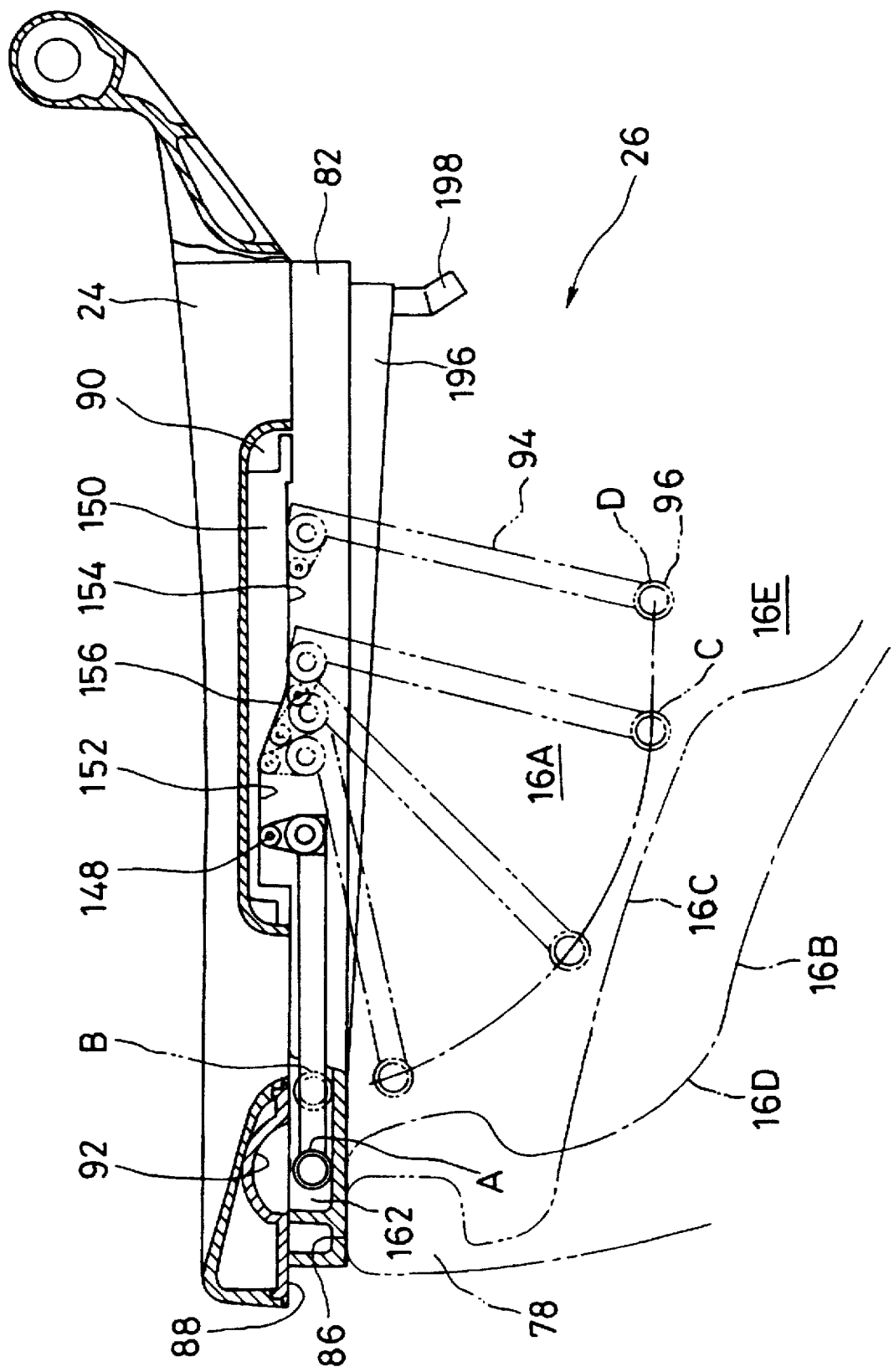
FIG. 9 is a schematic cross-sectional view taken along the line IX—IX of FIG. 4 and showing the swing arm and the urine sampling vessel in various different positions.

Generally, in the illustrated embodiment, the drive 98 for the swing arm 94 is adapted to impart a rotational movement as well as a translational movement to the swing arm 94 so as to move the urine sampling vessel 96 from the storage position situated underneath the frontal part of the toilet seat to various urine sampling positions, and vice versa, as best shown in FIG. 9.

More specifically, referring to FIGS. 3–6, the drive 98 is arranged on the frame 82 of the sampling apparatus suitably fixed to the underside of the toilet seat 24 by screws, for example. The drive 98 includes a slider 132 slidably mounted to the frame 82, the slider being guided for sliding movement parallel to the central plane of the bowl fixture 12 by a pair of guide rails 134 secured to the frame 82. Secured to the slider 132 is a rack 136 with which is engaged a pinion 140 mounted to the output shaft of a stepping motor 138 provided with a reduction gear mechanism and fixed to the frame 82. Accordingly, rotation of the motor 138 in either direction will cause back-and-forth translational movement of the slider 132. The motor 138 is controlled by the control circuit, described later.

The swing arm 94 is rotatably journaled to the slider 132 and is supported by the slider for sliding movement conjointly therewith. To this end, the slider 132 is provided with a pair of trunnion bearings 142 as shown in FIG. 5 to rotatably support the spindle 106 of the swing arm 94. The spindle 106 has an axial bore through which the flexible tube 122 and the lead wires 130 are extended.

The drive 98 is further provided with a lever and cam mechanism 144 that controls the angular position of the swing arm 94 in such a manner that the angular position of the urine sampling vessel 96 is in turn controlled in response to the back-and-forth movement of the slider 132 caused by rotation of the motor 138. As best shown in FIG. 5, a lever 146 is mounted over the spindle 106 of the swing arm 94 between the bearings 142 for rotation integrally with the spindle and a cam follower 148 in the form of a roller is supported at the end of the lever 146. The cam follower 148 is adapted to cooperate with a camplate 150 suitably secured to the frame 82 by screws and the like, the cam plate 150 being formed with a pair of staggered horizontal cam surfaces 152 and 154 and an inclined cam surface 156. An end of a coiled return spring 158 is fixed to the spindle 106 of the swing arm 94, the other end thereof being engaged with the bearing 142. The return spring 158 is preloaded such that the swing arm 94 is biased in the clockwise direction as viewed in FIG. 9. The initial angular position of the swing arm 94 is dictated by a stopper, not shown.

Figure 6:
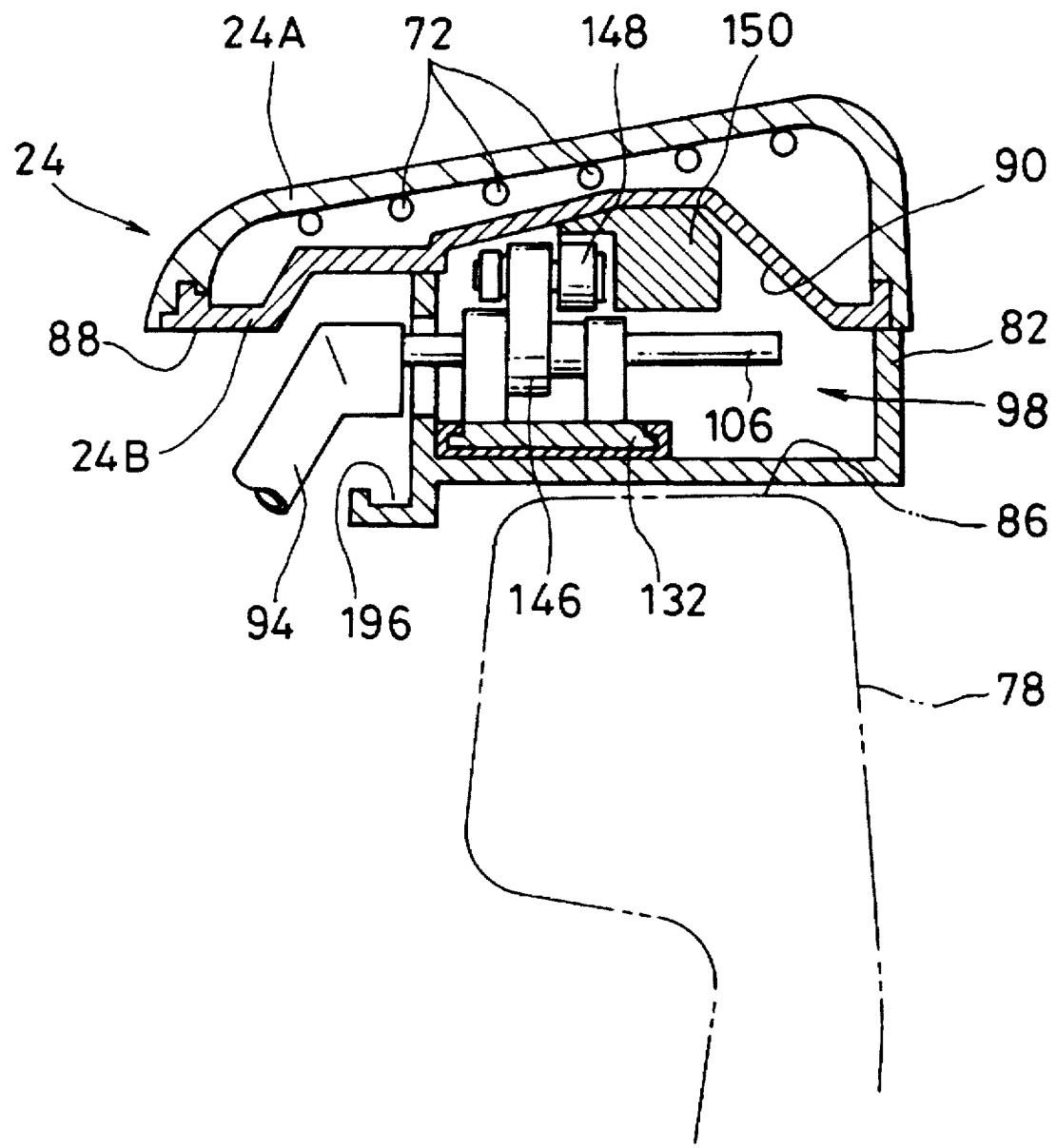
FIG. 6 is a cross-sectional view taken along the line VI—VI of FIG. 4.

The frame 82 carrying the swing arm 94 and the associated drive 98 of the urine sampling apparatus 26 is rigidly secured to the toilet seat 24 by screws and the like to form the integral toilet seat assembly 28 incorporating the urine sampling apparatus. As the toilet seat 24 is formed on the underside thereof with the prefabricated concavity 90 that corresponds in shape to the drive 98 as shown in FIGS. 3, 6 and 9, the component parts of the drive 98 such as the motor 138, the pinion 140, the camplate 150, the lever 146 and the cam follower 148 are accommodated partly in this concavity 90. As in this manner the space available in the toilet seat 24 is effectively utilized to accommodate the component parts of the urine sampling apparatus 26, it is possible to implement these component parts in a robust design. The toilet seat 24 provided with the concavity 90 may be manufactured on a mass production basis by using injection molds and the toilet seat assembly 28 may be assembled by incorporating the urine sampling apparatus 26 the rein.

Referring primarily to FIG. 9, the operation of the urine sampling apparatus 26 will be described. When the urine sampling apparatus 26 is not in use, the slider 132 is in the forward-most position so that the cam follower 148 is engaged with the first horizontal cam surface 152 of the camplate 150. As a result, the swing arm 94 is swung up under the action of the return spring 158 so that the urine sampling vessel 96 is held underneath the toilet seat 24 in the rest or storage position (position A) situated within the frame 82. With the urine sampling vessel in this position, the toilet seat assembly 28 may be swung up or down whenever the toilet is to be used for the purposes of routine excretion.

When the user is seated on the toilet seat 24 for the purposes of sampling and analysis of urine and turns on a start switch of the control unit 32, the motor 138 is rotated causing the rack and pinion mechanism 140/136 to commence the retracting movement of the slider 132 whereby the urine sampling vessel 96 is first pulled out horizontally and rearwardly from the storage position. As the cam follower 148 engages the inclined cam surface 156 of the camplate 150, the lever 146 starts to rotate the swing arm 94 (position B). As the cam follower 148 rides further on the inclined cam surface 156, the swing arm is moved backward while being rotated so that the urine sampling vessel 96 is displaced along the arcuate path or locus composed of the rotational movement and the translational movement as shown in FIG. 9. As the motor 138 rotates further, the cam follower 148 comes to engage the second horizontal cam surface 154 of the cam plate 150 (position C), whereupon the swing arm 94 commences translational movement while retaining its angular position until it is brought to the rear extremity position D.

The locus of the sampling vessel 96 may be modified as required by changing the cam profile of the camplate 150. For example, where the bowl fixture 12 has a low or depressed bowl surface configuration as shown by the dotted line 16B in FIG. 9, the cam profile may be designed such that the translational movement of the sampling vessel is commenced only after rotation for an adequate angle as shown. Alternatively, in the case of a raised bowl surface configuration as shown by the dotted line 16C, the cam profile may be selected such that the angle of the rotational movement is reduced as compared with the locus shown in FIG. 9 and the stroke of the translational movement is extended. In this manner, the path or locus of the sampling vessel can be altered simply by replacement of the camplate 150. As the path of the sampling vessel may readily be adapted in conformity with any bowl surface configuration, the urine sampling apparatus 26 according to the invention may be installed on any type of standard bowl fixture commercially available on the market.

It will be noted that, generally, the direction of urination is susceptible to fluctuate depending on the difference in the sexuality of the user so that in the case of a male the urine column tends to fall relatively forwardly in contrast to a female whose urine column tends to fall rearwardly. In addition, the direction of urination varies from individual to individual. Accordingly, it is preferable that the control switches for the motor 138 as well as the control circuit be arranged and designed such that, in the case of a male, the urine sampling vessel 96 is automatically brought to a predetermined position between the positions B–C, whereas in the case of a female, the urine sampling vessel 96 is automatically brought to a predetermined position between the positions C–D, as well as in such a manner that the user is permitted to finely adjust the position of the urine sampling vessel. As the movement of the sampling vessel 96 between the positions B and C is dictated primarily by the rotational movement, the sampling vessel will depict a locus which is defined closely along the bowl surface configuration of the inclined front wall 16D of the bowl 16. Consequently, by positioning the sampling vessel 96 at an appropriate position between the positions B and C, sampling of urine from a male user may be readily carried out. Between the positions C and D, on the other hand, the sampling vessel will undergo the horizontal translational movement to depict a path which follows the surface configuration of the bowl bottom region situated between the inclined front wall 16D and the discharge well 16E. This is suitable for sampling of urine from a female user.

As in this manner the sampling vessel 96 is movable back and forth for a wide range along the bowl surface, the sampling vessel 96 can be brought to an optimum sampling position regardless of whether the user is male or female. As a result, urine can be sampled without failure even if the user urinates with an easy natural posture.

The user may commence urination toward the urine sampling vessel 96 as it is brought to an appropriate position. Because the sampling vessel 96 is transversely elongated and is held to extend perpendicular to the vertical central plane 12A of the bowl fixture, the urine collecting trough 110 may be implemented in such a form as to provide a transverse extent in the range of 5–10 cm, for example, in the direction transverse to the direction of urination. Accordingly, even though the direction of urination is deviated laterally to some degree with respect to the vertical central plane of the bowl fixture, there is a high probability for the urine column to fall within the coverage of the transverse extent of the urine collecting trough 110. As a result, urine is effectively sampled.

Urine impinged upon the urine sampling vessel 96 will flow down along the trough 110 to accumulate in the urine pool 118. Urine thus sampled is sucked through the L-shaped suction pipe 124 and the flexible tube 122 by the urine syringe pump 52 arranged in the housing 22. The urine sample is then transferred to the urinalysis device 50 together with the carrier liquid in the reservoir 54 and is subjected to the quantitative analysis. Suction of the urine sample may be commenced automatically when, based on the signal from the electrodes 126 and 128, it is detected that urine has accumulated in the urine pool 118 up to the level of the upper electrode 128.

Upon completion of sampling and transfer of urine to the urinalysis device, the motor 138 is rotated in a direction to move the slider 132 forward whereby the urine sampling vessel 96 is returned to the position B in response to the advance and upward rotation of the swing arm 94 and is thereafter returned to the storage position A in response to the translational movement of the swing arm. The urine sampling vessel 96 stands by in this position. As the urine sampling vessel 96 is designed in an elongated form, it can be readily stored in a vertically narrow defined between the lower surface 88 of the toilet seat 24 and the upper surface 86 of the rim 78 of the toilet bowl fixture as shown in FIG. 9. As the sampling vessel 96 is thus moved to and away from the storage position by the horizontal translational movement and is concealed underneath the toilet seat 24 when not in use, the toilet is easy to use when served for the purposes of routine excretion.

It is desirable that after urine sampling, the urine sampling vessel 96 soiled by urine be washed with water. To this end, the frame 82 is provided with a housing 160 which cooperates with the lower surface of the seat 24 to form a washing chamber 162 as shown in FIGS. 3, 4, 10 and 11. A swingable cover 164 is pivoted to the washing chamber housing 160 to open and close the gateway or entrance to the washing chamber 162. The cover 164 is biased by a coiled spring 166 to a normally open position but is adapted to be closed by an actuating mechanism 168 interlocked with the slider 132.

Figure 10:
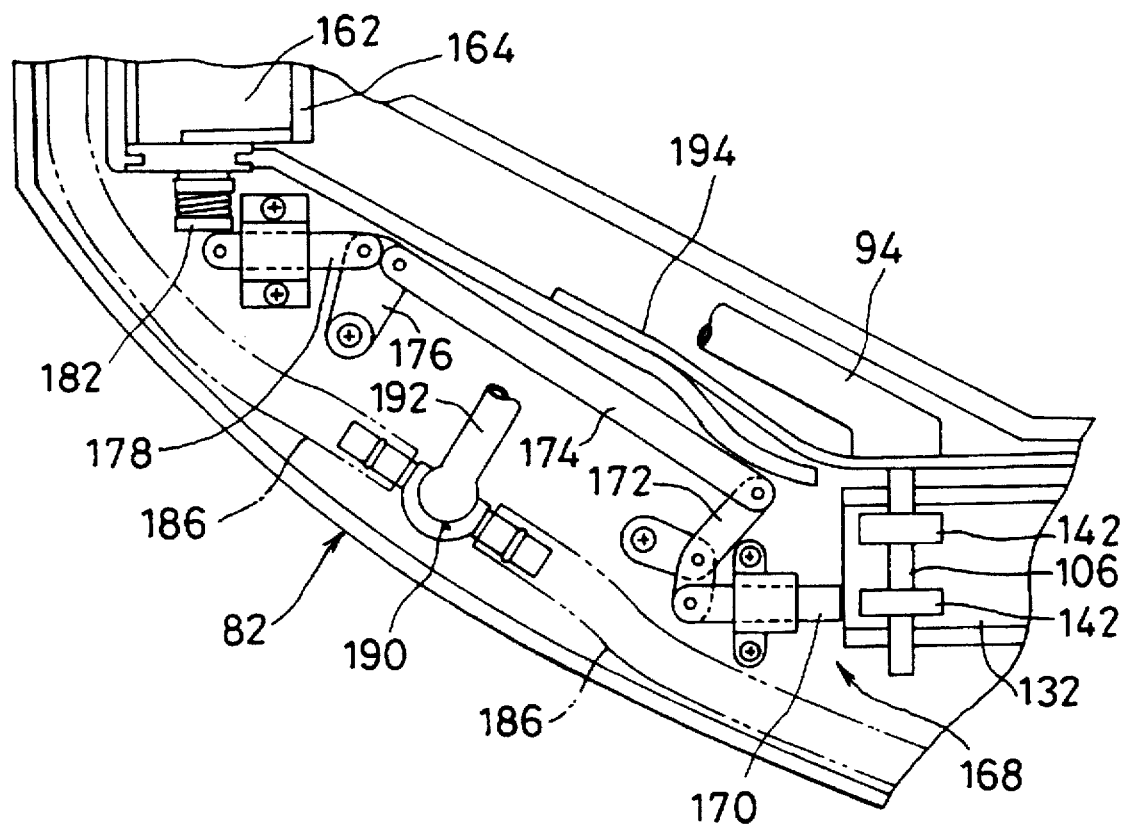
FIG. 10 is a plan view, partly cut away, of an actuating mechanism for a washing chamber cover shown in FIG. 3.
Figure 11:
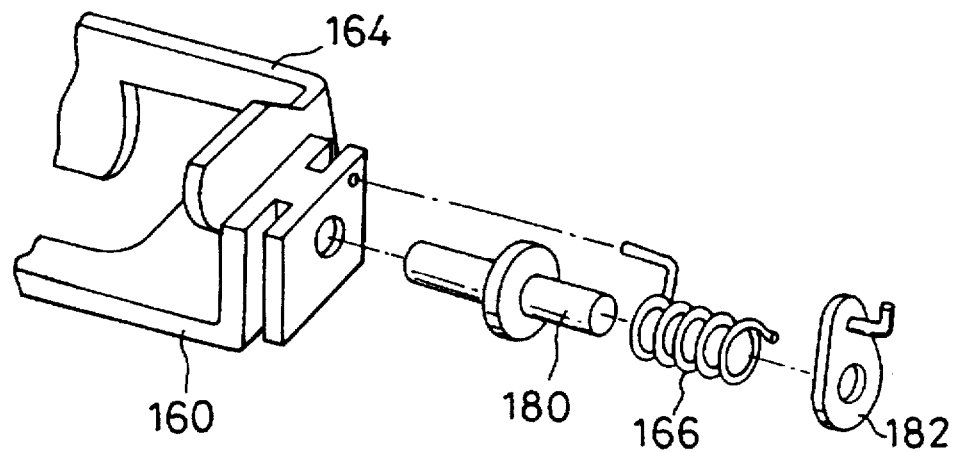
FIG. 11 is an exploded perspective view showing a part of the actuating mechanism for the washing chamber cover.

As shown in FIGS. 10 and 11, the actuating mechanism 168 includes a push rod 170 adapted to be engaged by the slider 132, a pivoting lever 172, a link 174, another lever 176, a slidable bar 178, and a lever 182 rotatable integrally with a pivot 180 for the cover 164, the arrangement being such that the cover 164 is opened as the sampling vessel 96 moves out of the washing chamber 162 in response to the backward movement of the slider 132 and that the cover 164 is closed against the bias of the spring 166 when the sampling vessel 96 is returned to the storage position in the washing chamber in response to the forward movement of the slider 132. As will be apparent from FIG. 9, the cover 164 is rotated by making use of the concavity 92 formed on the toilet seat 24.

Figure 4:
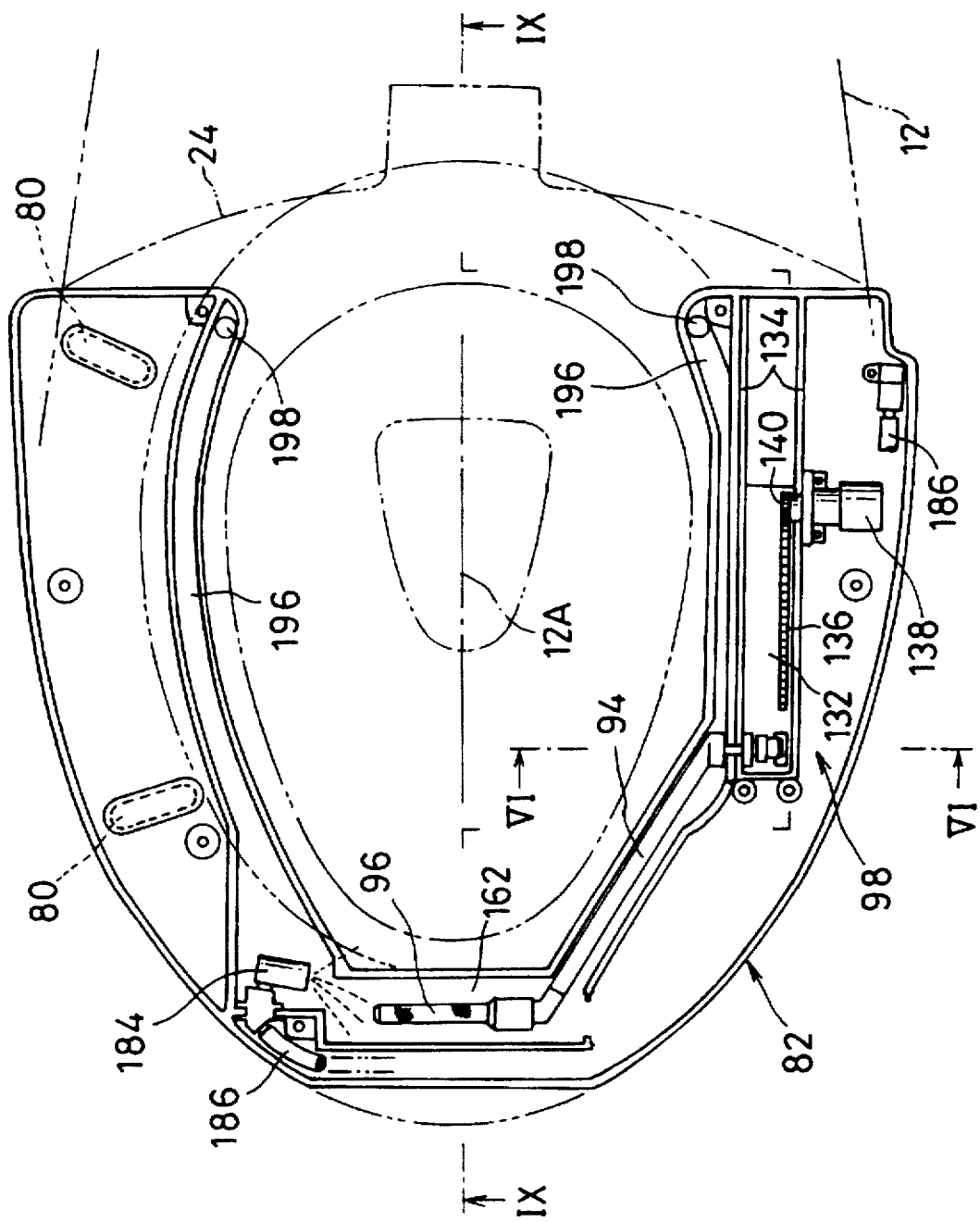
FIG. 4 is a plan view of the urine sampling apparatus of the toilet seat assembly shown in FIG. 3, with the toilet seat, a cam plate and a swingable cover being removed and with the toilet seat and the toilet bowl fixture being shown by the phantom line and the dotted line, respectively.
Figure 5:
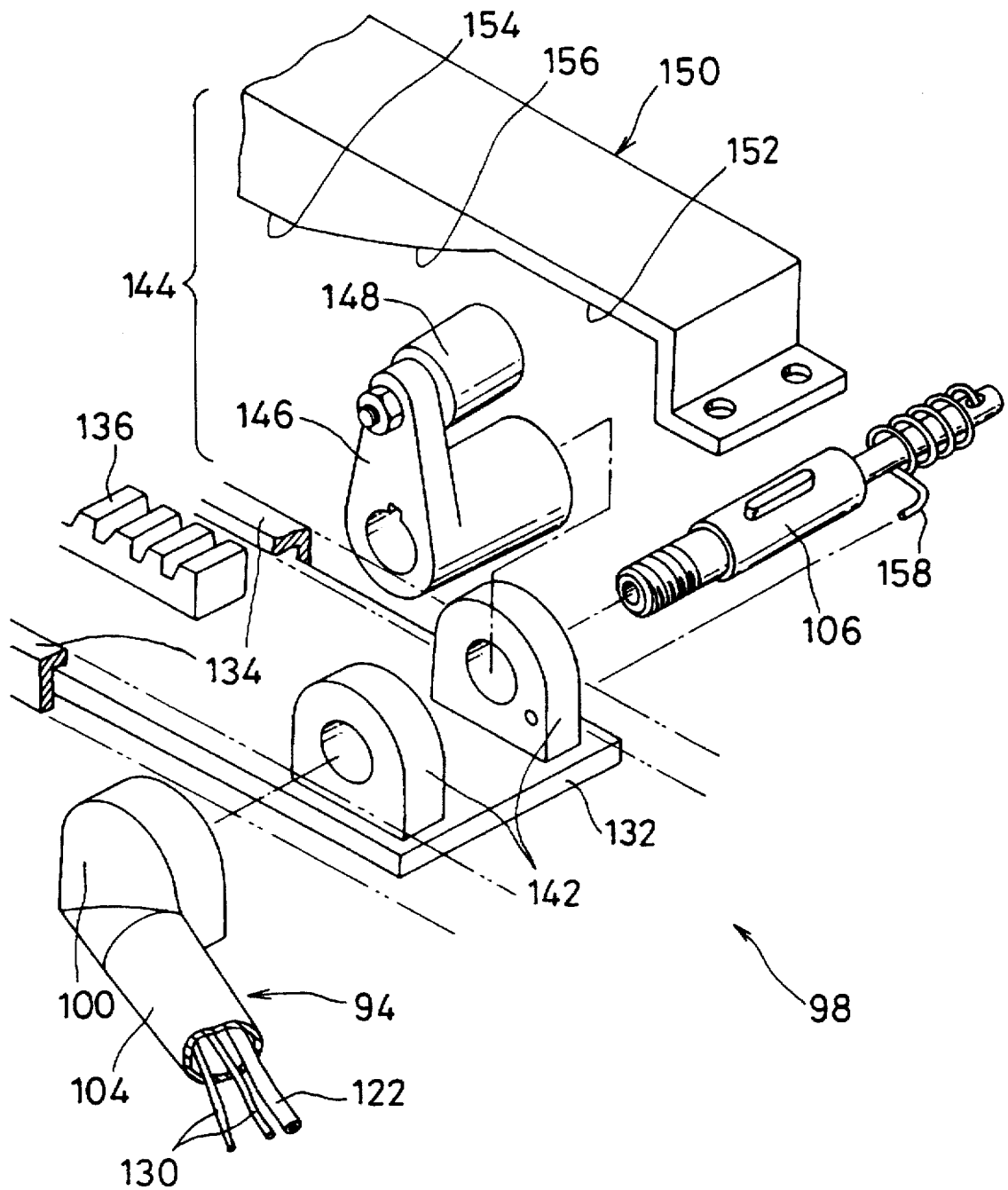
FIG. 5 is an enlarged exploded perspective view, partly cut away, of a part of the swing arm drive shown in FIGS. 3 and 4.

As best shown in FIGS. 3 and 4, a spray nozzle 184 is arranged and directed toward the washing chamber 162 to eject water toward the sampling vessel 96 as placed in the storage position. The spray nozzle 184 may be connected through a hose 86 and a solenoid valve, described later, to a water line 188 (FIG. 1) to supply water under pressure. Alternatively, the hose 186 may be connected to a water supply valve of the bidet system 62. As the sampling vessel 96 is returned after sampling into the washing chamber 162, the solenoid valve is opened to supply water under pressure to the spray nozzle 184 whereby the sampling vessel 96 is washed and cleansed. During washing, the gateway to the washing chamber is closed by the cover 164 so that water is prevented from splashing outwardly of the washing chamber. Water ejected from the spray nozzle will be rebounded by the wall of the narrow washing chamber to effectively cleanse the sampling vessel 96. Since the sampling vessel 96 is washed in this manner each time after use, a fresh urine specimen is obtainable so that a high degree of urinalysis is performed. Because the spray nozzle 184 is arranged laterally of the sampling vessel 96 in generally the same horizontal plane as the sampling vessel, it is possible to arrange the spray nozzle 184, and to store the sampling vessel 96, within the washing chamber 162 of a limited vertical dimension confined between the rim 78 of the bowl and the toilet seat 24. Accordingly, the urine sampling apparatus 26 can be made compact.

As shown in FIGS. 3 and 10, the water supply hose 186 may be provided with a T-joint 190 to which is connected a T-shaped spray nozzle 192 disposed above the swing arm 94. With this arrangement, the swing arm 94 is washed simultaneously with washing of the sampling vessel 96. A strip 194 of flexible plastic material may be engaged with the spindle 106 of the swing arm 94 to prevent water sprayed by the swing arm washing nozzle 192 from entering into the drive 98 and to protect the latter against water.

Figure 12:
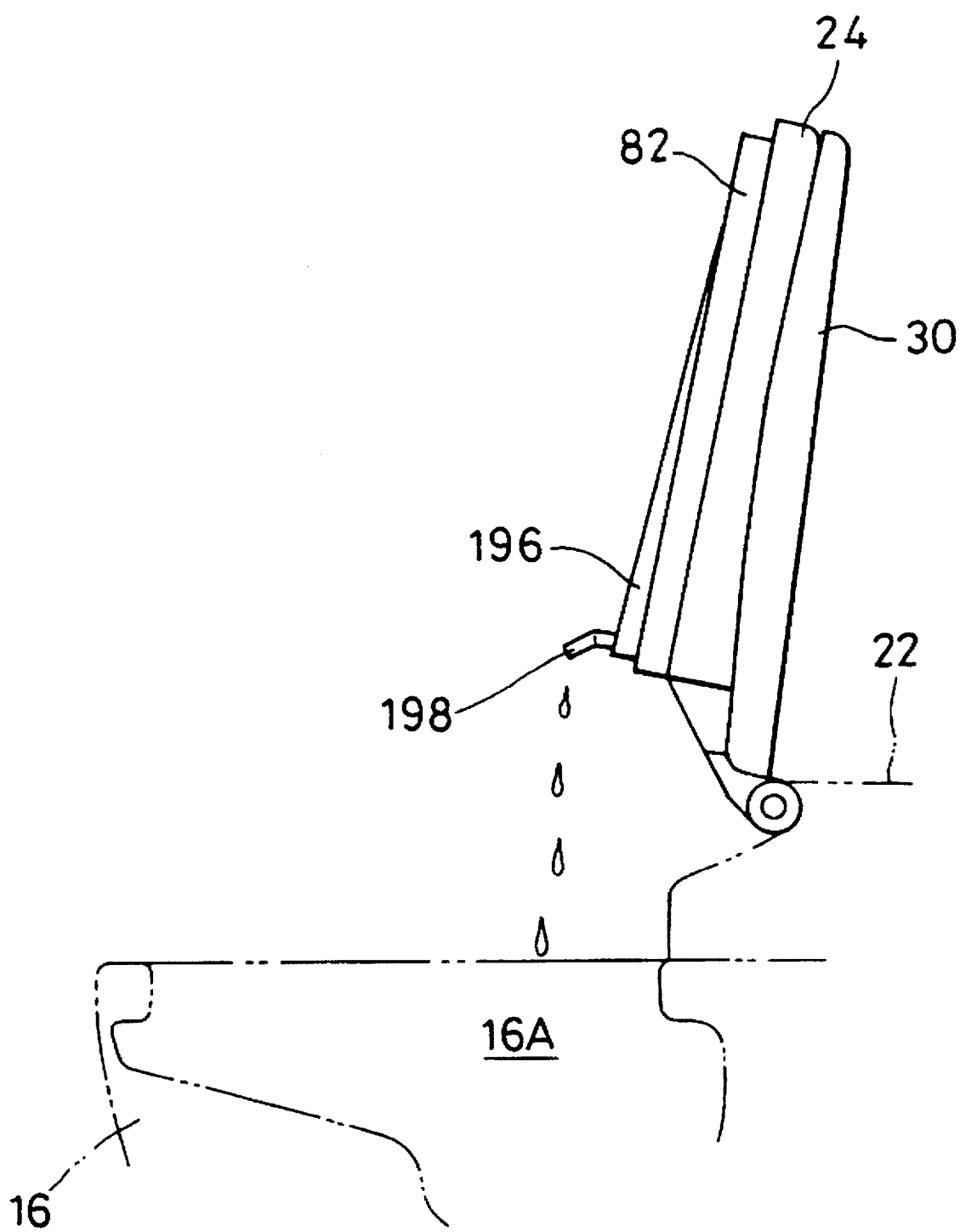
FIG. 12 is a schematic elevational view showing the toilet seat in its swung-up position.

Used washing water is discharged into the toilet bowl 16. To this end, the frame 82 of the sampling apparatus is provided with a pair of drainage troughs 196 extending rearwardly from the washing chamber 162 along the sides of the rim 78, as shown in FIGS. 3 and 4. These drainage troughs 196 are inclined rearwardly and downwardly as best shown in FIG. 9 and are communicated at the rear ends with slanted drainage pipes 198 mounted to the frame 82. Accordingly, when the toilet seat assembly 28 is in the horizontal position, water ejected from the spray nozzle 184 will flow rearwards along the inclined drainage troughs 196 and will be discharged into the bowl 16 through the drainage pipes 198. Therefore, the sampling vessel 96 and the swing arm 94 may be washed even when the user is seated on the toilet seat. As shown in FIG. 12, the drainage pipes 198 are so arranged as to project over the bowl when the toilet seat is swung up. Consequently, when the toilet seat 24 is swung up, any droplets of residual washing water remaining in the troughs 196 will be drained into the bowl 16 thereby avoiding fouling of the toilet floor.

As shown in FIG. 3, the frame 82 is provided at its rear end with a recess 200 in which an adapter or grommet 202 is fitted, the flexible tube 122 and the lead wires 130 extending from the swing arm 94 as well as the water hose 186 being arranged to extend through the adapter. Due to the presence of the adapter 202, the arrangement of the piping and wiring between the urine sampling apparatus 26 and the housing 22 is simplified and any damages that would otherwise occur on the piping and wiring during swinging of the toilet seat assembly 28 is avoided.

Figure 13:
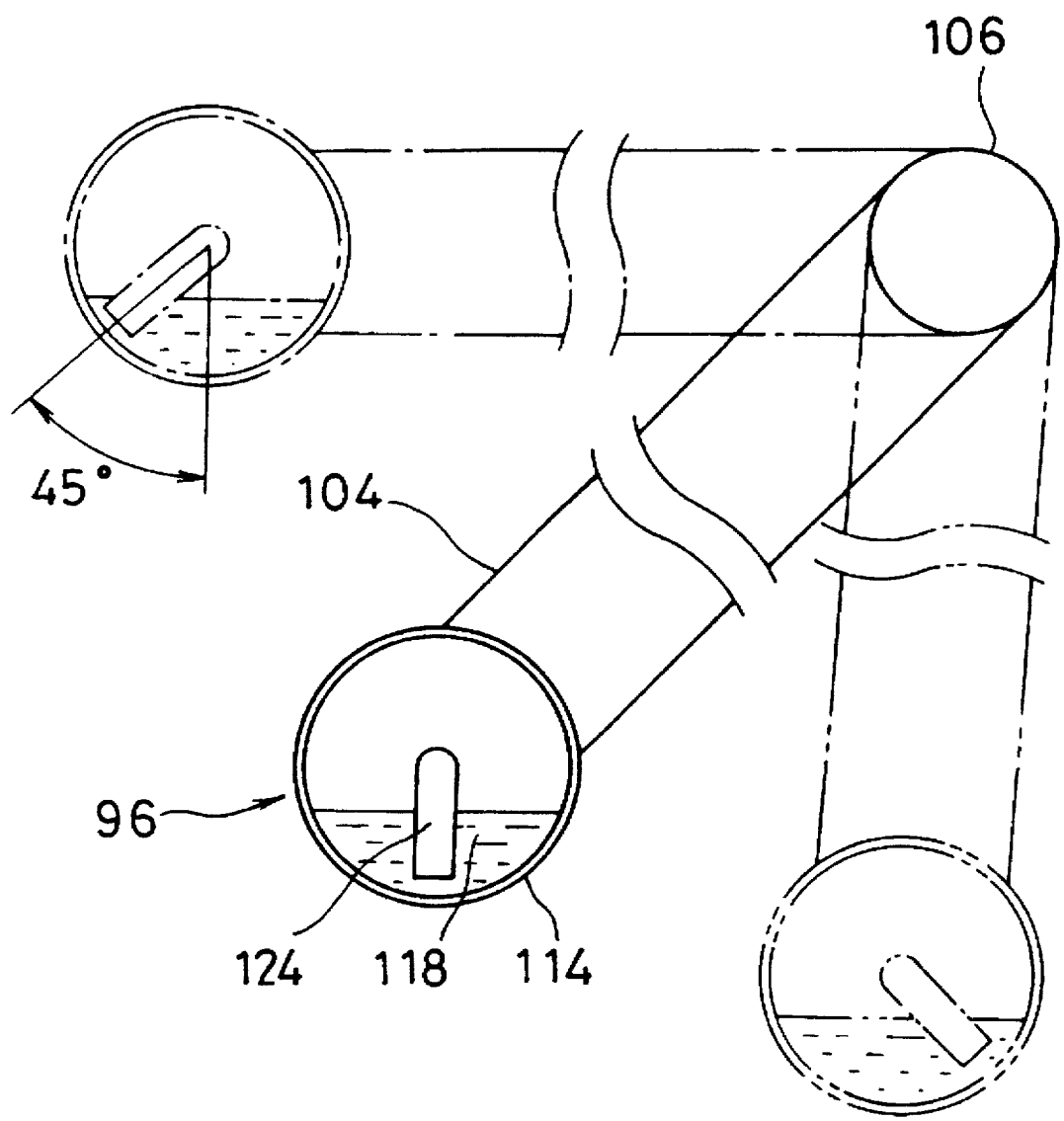
FIG. 13 is a schematic cross-sectional view taken along the line XIII—XIII of FIG. 8 and schematically showing the inclination of a urine suction pipe under different angular positions of the swing arm.

As described before with reference to FIG. 9, the swing arm 94 is adapted to be rotated for about 90° between the horizontal angular position B and the roughly vertical position C to ensure that, in the case of a male user, suction of urine through the suction pipe 124 is primarily carried out with the sampling vessel being positioned at an appropriate angular position between the positions B–C, urine sampling for a female user being preferably carried out with the sampling vessel positioned at an appropriate position between the positions C–D. The angular position of the suction pipe 124 will be varied in response to the rotation of the swing arm 94. Accordingly, it is preferable that the suction pipe 124 be arranged at such an angle that it is directed downwards substantially vertically when the swing arm 94 is rotated at an angle of about 45°, as shown in FIG. 13. With this arrangement, the inlet of the suction pipe 124 will be located generally at the bottom of the urine pool 118 regardless of the variation in the angular position of the sampling vessel 96 resulting from the difference in the sexuality of the user. This advantageously permits to draw urine free from air bubbles. It will also be noted that when the sampling vessel 96 is stored in the storage and washing chamber 162, the inclination of the suction pipe 124 with respect to the vertical will be no greater than 45°. Accordingly, after washing of the sampling vessel, it is possible to suck and remove most of the residual water remaining in the urine pool 118 by operating the syringe pump 52 to apply a vacuum to the suction pipe 124. Suction of the residual water is advantageous in preventing clogging of urine sample transfer conduit as well as in preventing urine sample from being diluted by the residual water during subsequent sampling.

Figure 14:
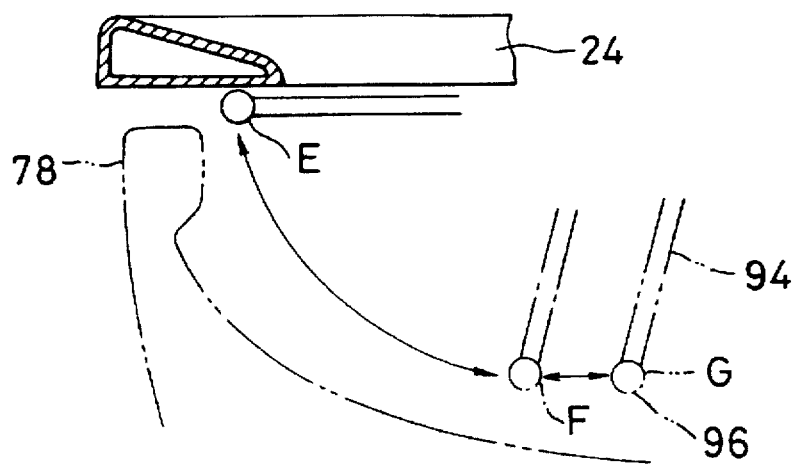
FIGS. 14–16 are schematic views showing various paths of the urine sampling vessel.
Figure 15:
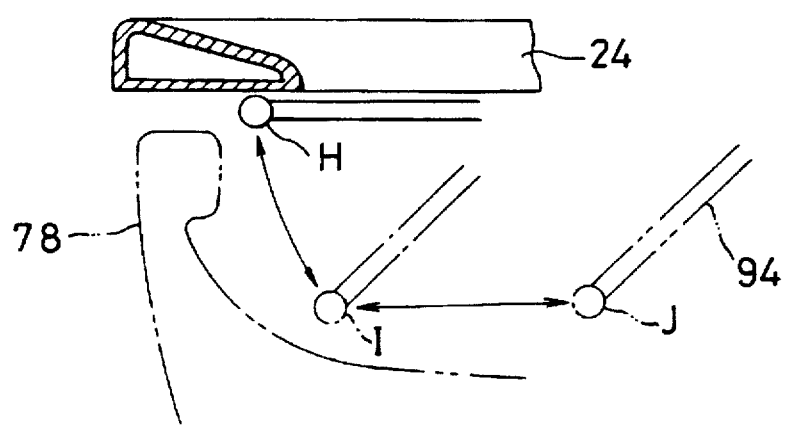
Figure 16:
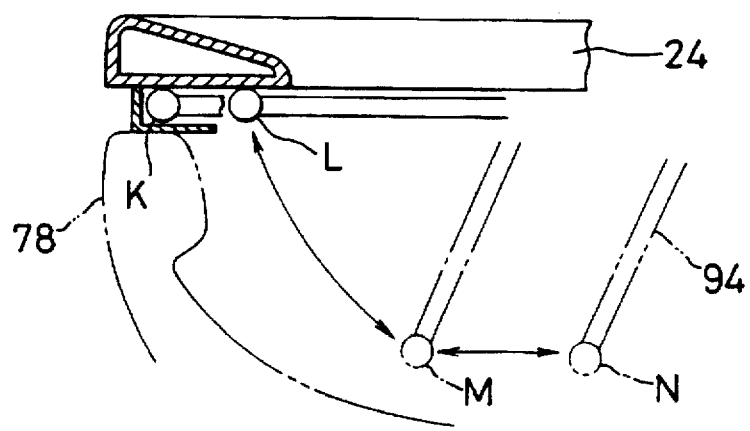

In FIGS. 14–16, there are schematically shown different modes of movement of the swing arm 94 and the sampling vessel 96. In the mode shown in FIG. 14, the sampling vessel 96 when not in use is concealed under the toilet seat 24 and is placed at a storage position E situated inwardly of the inner periphery of the rim 78. The sampling vessel 96 is moved from the position E to the position F by the rotational and translational movements and is moved from the position F to the position G only by the translational movement. Such movement may be given to the sampling vessel 96 by eliminating or disabling the first horizontal cam surface 152 of the camplate 150.

In the mode shown in FIG. 15, the sampling vessel 96 is displaced between the storage position H and the operating position I only by the rotational movement and is displaced between the positions I and J only by the horizontal translational movement. In this mode, necessary movement may be given to the sampling vessel 96 by directly rotating the swing arm 94 by means of a separate motor and by translating the slider 132 by means of a pinion and rack mechanism, a pulley and belt mechanism, a lead screw mechanism, a hydraulic cylinder mechanism or a solenoid mechanism.

In the mode illustrated in FIG. 16, the sampling vessel 96 is moved only by the horizontal translational movement between the positions K and L, only by the rotational movement between the positions L and M, only by the horizontal translational movement between the positions M and N. Such movement may be generated by the combination of a rotary drive mechanism such as a motor and a translational drive mechanism such as a pinion and rack mechanism.

Figure 17:
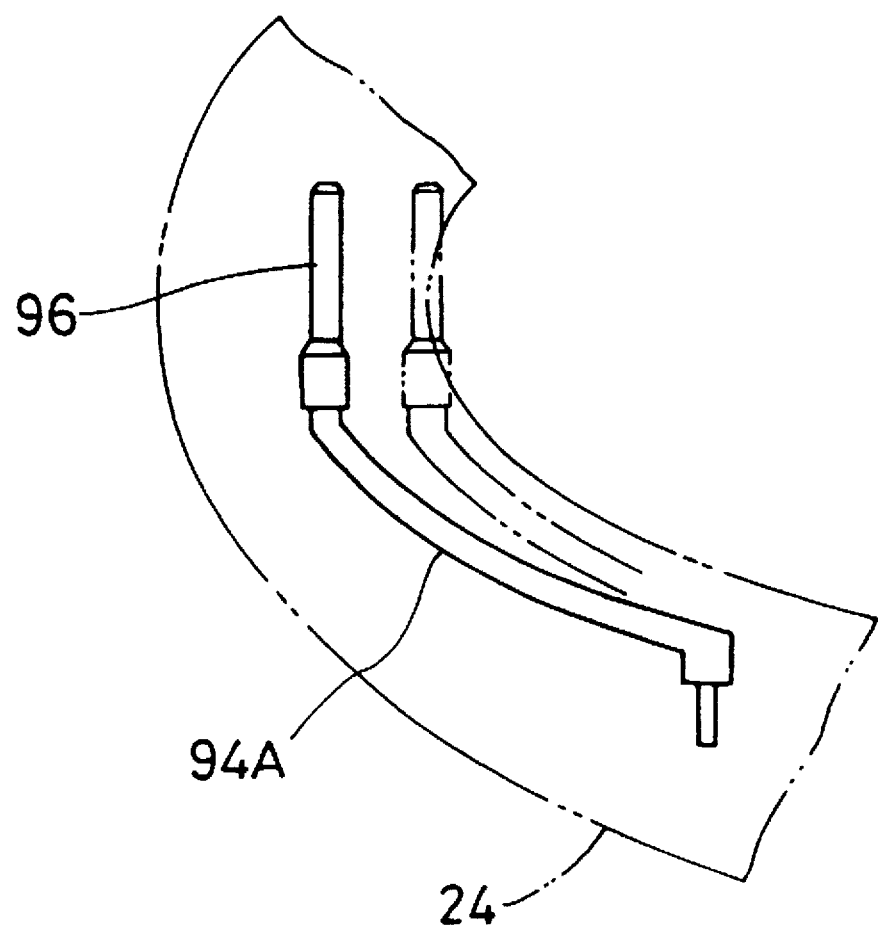
FIG. 17 is a plan view showing a modified form of the swing arm.

FIG. 17 shows a modified form of the swing arm 94. In this form, the swing arm 94A is curved so as to conform with the inner contour of the toilet seat. With this arrangement, the swing arm will remain concealed under the toilet seat 24 when it is pulled rearwardly from the storage position to the position in which rotation of swing arm takes place. Therefore, there is no risk that the swing arm is brought in contact with the thigh of the user.

Figure 18:
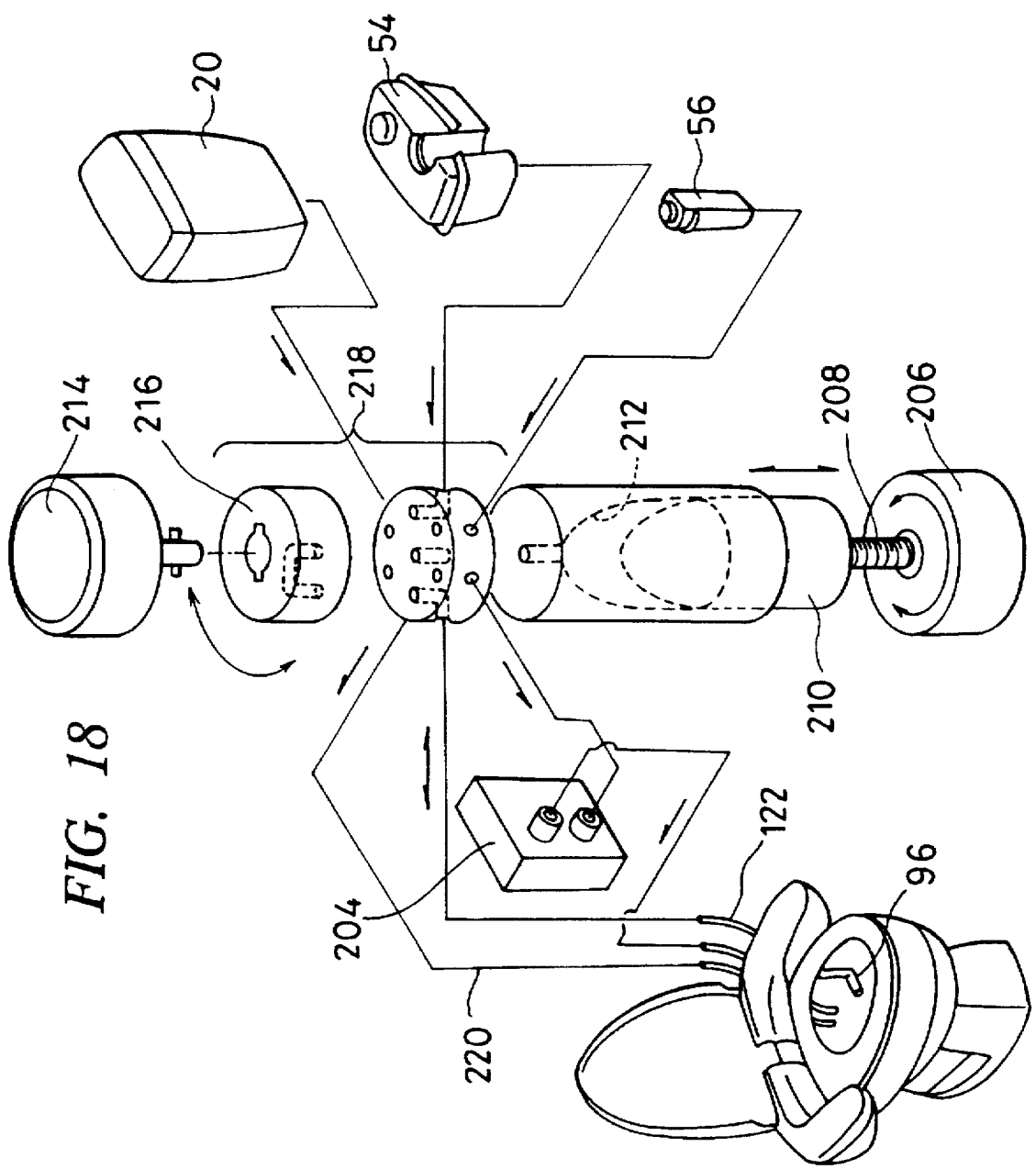
FIG. 18 is a schematic view showing a fluid transfer system of the urinalysis unit shown in FIG. 1.

Referring to FIG. 18, other components of the urinalysis unit 14 incorporating the urine sampling apparatus 26 according to the invention will be briefly described. The electrically driven syringe pump 52 is designed to transfer the urine sample as sampled by the sampling apparatus 26 and a carrier liquid to a polarographic flow cell 204 of the urinalysis device 50. As the syringe pump 52 and the flow cell 204 do not form part of the invention, they need not be described in any detail. Briefly, the syringe pump 52 includes a piston 210 reciprocated by a stepping motor 206 and a lead screw mechanism 208 so as to draw and deliver a fluid into and out of a pumping chamber 212. Coupled to the syringe pump 52 is a rotary valve 218 having a rotary disc 216 driven by another stepping motor 214. The rotary valve is adapted to selectively connect the pumping chamber 212 of the syringe pump 52 to the flexible tube 122 from the carrier liquid reservoir 54, the reservoir for the calibration solution, the cistern 20, or a discharge conduit 220. The flow cell 204 may be designed, for example, to carry out quantitative analysis of glucose contained in the urine sample by way of the polarographic process. A control circuit 222 for controlling the urine sampling apparatus 26, the syringe pump 52, the rotary valve 218 and the flow cell 20 may be mounted to a circuit board of the urinalysis device 50 as shown in FIG. 2.

Figure 19:
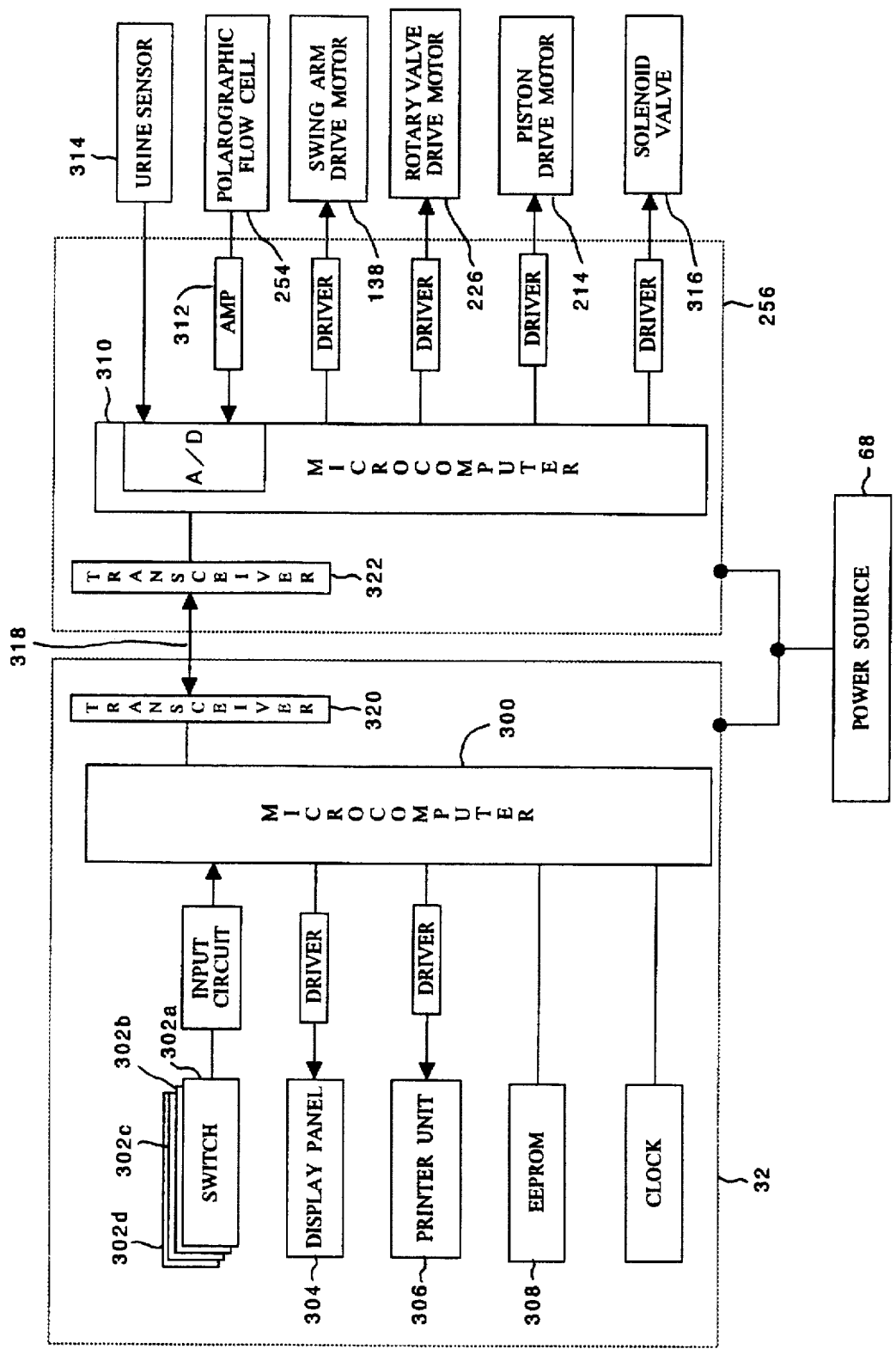
FIG. 19 is a block diagram of a control unit and a control circuit of the urinalysis unit shown in FIG. 1.

FIG. 19 illustrates examples of the control unit 32 and the control circuit 222. The control unit 32 installed on the side wall of the toilet may comprise a programmed microcomputer 300, a plurality of control switches 302, a liquid crystal display panel 304 for displaying various instructions to the user and the results of urinalysis, a printer unit 306 for outputting the results of urinalysis and the trends of data, and a flash memory device 308 for storing the data of urinalysis. The control switches 302 may separately include a urinalysis start switch 302a for male and a urinalysis start switch 302b for female, the arrangement being such that when the male's switch 302a is depressed the urine sampling vessel 96 is automatically brought to a predetermined male's sampling position (e.g., an appropriate position between the positions B–C of FIG. 9) and that when the female's switch 302b is depressed the urine sampling vessel is brought to a predetermined female's sampling position (e.g., an appropriate position between the positions C–D). The control switches 302 may further include a pair of fine adjustment switches 302c and 302d for finely displacing the urine sampling vessel 96 in the fore-and-aft direction with respect to the predetermined male's or female's position in response to the instructions of the user.

The control circuit 222 includes a microcomputer 310 which is so programmed as to control the sampling apparatus 26 and the other components of the urinalysis unit 14 in a manner shown in the flowchart described later. The output of the polarographic cell 204 is amplified by an amplifier 312 and is fed to an analog-to-digital (A/D) converter circuit of the microcomputer 310. A urine sensor 314 is adapted to monitor the electric resistance of the gap defined between the urine detection electrodes 126 and 128 of the urine sampling vessel 96 to see if urine has accumulated in the urine pool 118 of the sampling vessel 96, the output of the urine sensor being delivered to the A/D converter circuit of the microcomputer 310. The microcomputer 310 drives the swing arm drive motor 138, the rotary valve drive motor 214, piston drive motor 206, and a solenoid valve 316 for controlling supply of water to the spray nozzle 184, through respective driver circuits. The microcomputers 300 and 310 are connected with each other by a communication cable 318 to transfer data and signals via transceivers 320 and 322 by serial communication process.

Figure 20:
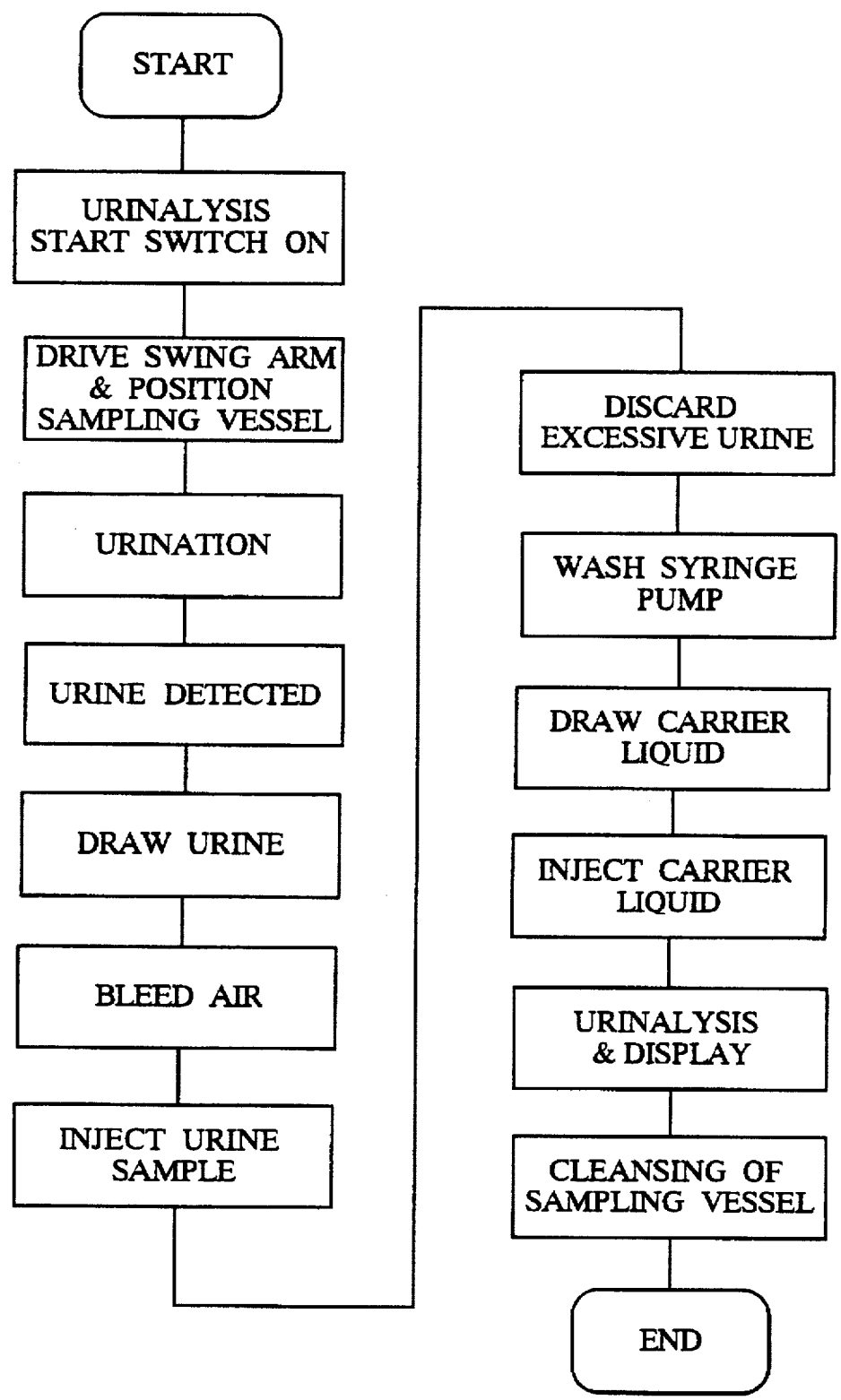
FIG. 20 is a flowchart showing the operation of the urinalysis unit shown in FIG. 1.

A mode of use and operation of the sampling apparatus 26 and the urinalysis unit 14 will be described by way of an example with reference also to the schematic view of FIG. 18 and the flowchart of FIGS. 20. As the user presses on the urinalysis start switch 302a or 302b, the microcomputer 310 drives the swing arm drive motor 138 to move the urine sampling vessel 96 to a predetermined urine sampling position and then places the sampling vessel 96 in a desired position in response to the fine adjustment switches 302c or 302d. As positioning of the sampling vessel is thus completed, the user may urinate toward the sampling vessel to have urine sampling started. As accumulation of urine in the urine pool 118 of the sampling vessel 96 is detected based on the signal from the urine sensor 314, the microcomputer 310 energizes the rotary valve drive motor 214 to connect the pumping chamber 212 of the syringe pump 52 to the sampling vessel 96. With the rotary valve in this position, the microcomputer 310 energizes the piston drive motor 206 of the syringe pump 52 to move the piston 210 on the downward stroke to cause about 2 ml, for example, of urine to be drawn into the pumping chamber of the syringe pump 52.

Then the rotary valve is again rotated so as to connect the syringe pump 52 to the discharge conduit 220. In this state, the piston drive motor 206 is energized to lift the piston of the syringe pump 52 so that a part of urine in the pumping cheer is discharged through the discharge conduit 220 into the bowl of the toilet bowl fixture 12. This permits air bleeding of the pumping cheer so that air bubbles are prevented from being forwarded to the polarographic flow cell 204 even in the event that air has been drawn in the pumping chamber together with urine sample.

The rotary valve is again driven until the pumping chamber 212 is connected to the polarographic flow cell 204. Then the piston of the syringe pump 52 is further lifted until about 10–20 μl of urine sample is injected toward the flow cell. The rotary valve is again rotated to connect the pumping chamber to the discharge conduit 220 whereupon the piston is lifted to the full stroke so as to evacuate the pumping chamber by discarding any excessive urine through the conduit 220 into the bowl 16.

The pumping chamber of the syringe pump 52 is rinsed with water after injection of urine sample. This is done by rotating the rotary valve to connect the pumping chamber of the syringe pump 52 with the cistern 20, by descending the piston to draw water from the cistern into the pumping chamber, by driving the rotary valve to connect the pumping chamber to the discharge conduit 220, and by lifting the piston. Rinsing of the pumping chamber may be carried out for more than a cycle.

Then the rotary valve is again rotated until the syringe pump 52 is connected to the carrier liquid reservoir 54. The carrier liquid in the reservoir 54 serves to transfer the urine sample to the polarographic flow cell 204 as well as to dilute the urine sample being delivered to the flow cell 204. The carrier liquid also serves as a buffer solution that provides buffer effect necessary for the stable operation of the polarographic flow cell. To this end, the carrier liquid may contain various additives including hydrogen ion concentration conditioning agent such as $KH_2PO_4$ and $Na_2HPO_4$, chlorine ion intensity conditioning agent such as KCl, and antiseptic. When the syringe pump 52 is connected to the carrier liquid reservoir 54 as mentioned before, the syringe pump 52 is operated to draw the carrier liquid from the reservoir 54 into the pumping chamber 212. The rotary valve is again rotated and the piston 210 is lifted to inject the carrier liquid toward the flow cell whereby 10–20 μl of previously injected urine sample is transferred to the polarographic flow cell 204 while being mixed with and diluted by the carrier liquid, the mixture traversed the flow cell being discharged into the bowl of the toilet. The speed of injection of the carrier liquid may be controlled such that the urine sample flows past the flow cell after it is diluted by the carrier liquid for at least 30 folds. The amount of injection of the carrier liquid may be selected to be about 2–4 ml per cycle. With this amount, the polarographic flow cell 204 will be filled again with fresh carrier liquid after the mixture of urine sample and carrier liquid has flown past the flow cell.

As the mixture of urine sample and carrier liquid flows past the polarographic flow cell 204, the flow cell will output an electric signal according to the glucose content in the mixture. The signal is amplified by the amplifier 312 and is sent to the A/D converter circuit of the microcomputer 310 for conversion into a digital datum which is transmitted to the microcomputer 300 of the control unit 32 by serial communication. The microcomputer 300 computes the urinal glucose content based on the digital datum representing the electric current and displays it on the display panel 304. The data of urinal glucose content are also stored in the flash memory 308. The microcomputer 300 is also programmed to derive the trend of urinalysis and to output it through the printer unit 306 in response to the instructions of the user.

Upon completion of urinalysis or urine sampling, the microcomputer 310 energizes the swing arm drive motor 138 to return the sampling vessel 96 to the storage position A shown in FIG. 9. Then the solenoid valve 316 is open to supply water under pressure to the spray nozzle 184 whereby the sampling vessel 96 is cleansed with water.

As urinalysis is repeated, the output of the polarographic flow cell 204 will be decreased as time elapses. Therefore, it is desirable to periodically calibrate the flow cell output. To this end, a calibration solution consisting of a standard glucose solution of a given known glucose concentration is stored in the reservoir 56 and is periodically forwarded to the flow cell in place of the urine sample to periodically detect and measure the flow cell output with respect to the standard glucose solution. During actual urinalysis, the flow cell output for the urine sample may be compensated for in accordance with the flow cell output with respect to the standard glucose solution to derive the urinal glucose content.

Figure 21:
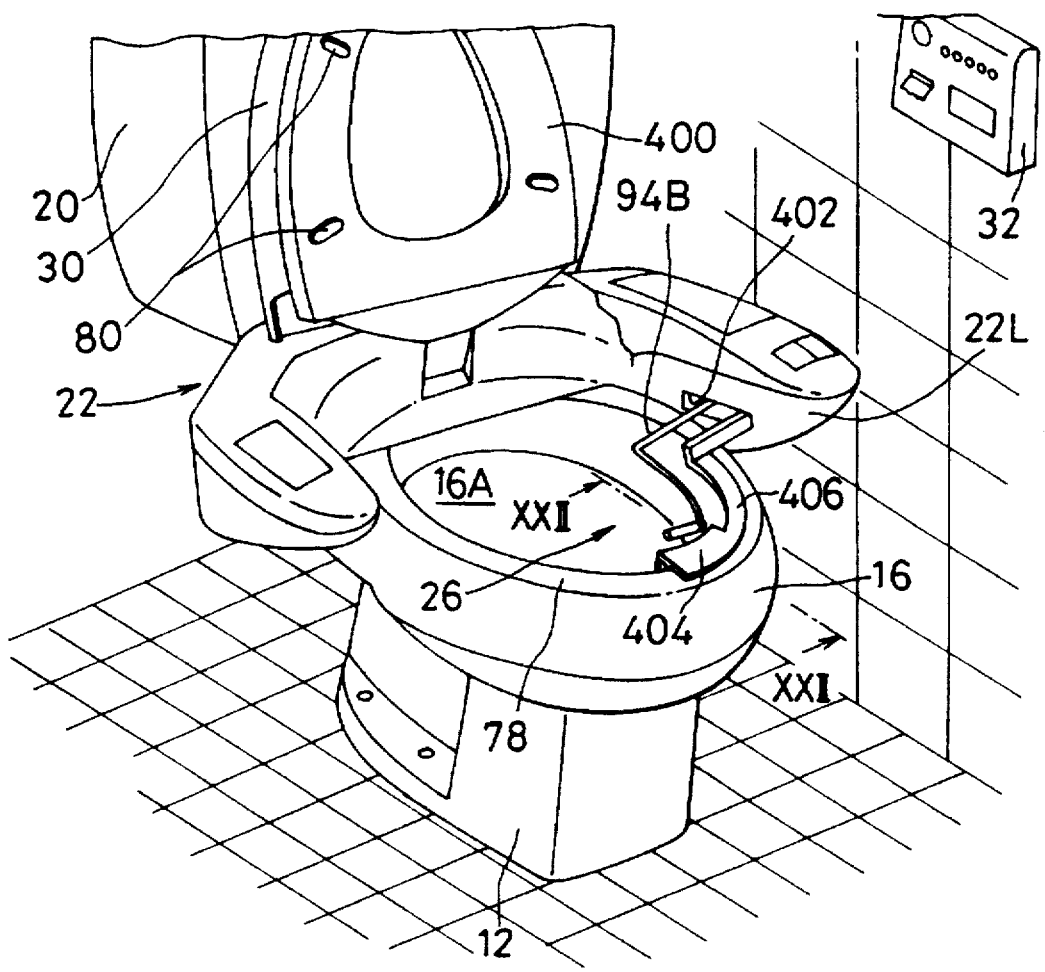
FIG. 21 is a perspective view, partly cut away, of the second embodiment of the urine sampling apparatus according to the invention, with the toilet seat being shown as being in its swung-up position.
Figure 22:
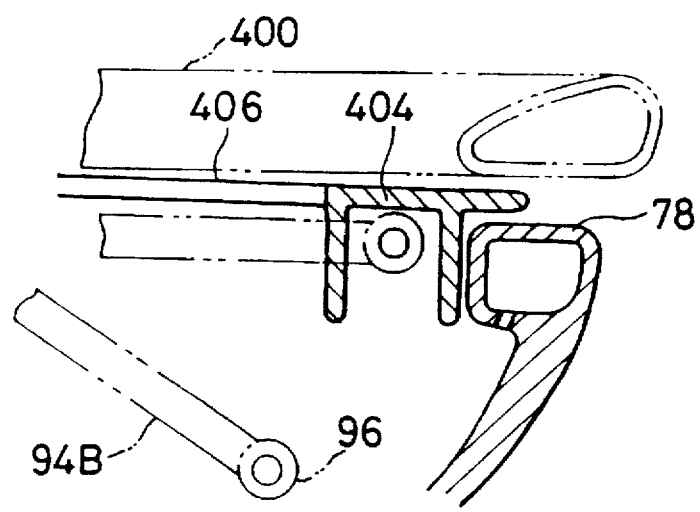
FIG. 22 is a cross-sectional view taken along the line XXII—XXII of FIG. 21.

Referring to FIGS. 21 and 22, the second embodiment of the urine sampling apparatus according to the invention will be described. The primary difference from the first embodiment described before is that the drive 98 of the sampling apparatus 26 is arranged in the left-hand lateral portion 22L of the housing. Accordingly, parts and members identical or similar to the foregoing first embodiment are indicated in FIG. 21 by like reference numerals and only the differences will be described. In this embodiment, a conventional toilet seat 400 is hinged to the housing 22. A swing arm drive, not shown, similar to the drive 98 of the first embodiment is mounted to the frame 34 of the housing 22 to move the sampling vessel 96 within the inner space of the bowl. The shaft of the swing arm 94B is made longer than that of the first embodiment so as to extend through a slot 402 formed in the housing lateral portion 22L and to project above the bowl 16 by overlying the rim 78 of the bowl fixture 12.

A case 406 provided with a storage and washing section 404 is mounted to the housing lateral portion 22L to store the swing arm 94B in its storage position and to wash the sampling vessel in that position. As shown in FIG. 22, the case 406 is situated inwardly of the rim 78 of the bowl fixture and is adapted to rest on the rim 78, the storage and washing section 404 being provided with a spray nozzle, not shown, similar to the nozzle 184 of the first embodiment. In the second embodiment, sampling of urine may be carried out by positioning the sampling vessel 96 by the rotational and translational movements of the swing arm 94B in a manner similar to the first embodiment. However, the sampling vessel 96 may be brought within the storage and washing section 404 only by the rotational movement of the swing arm and may be stored inwardly of the rim 78 as shown in FIG. 22. In other respects, the operation of the second embodiment is similar to the first embodiment and need not be described.

Figure 23:
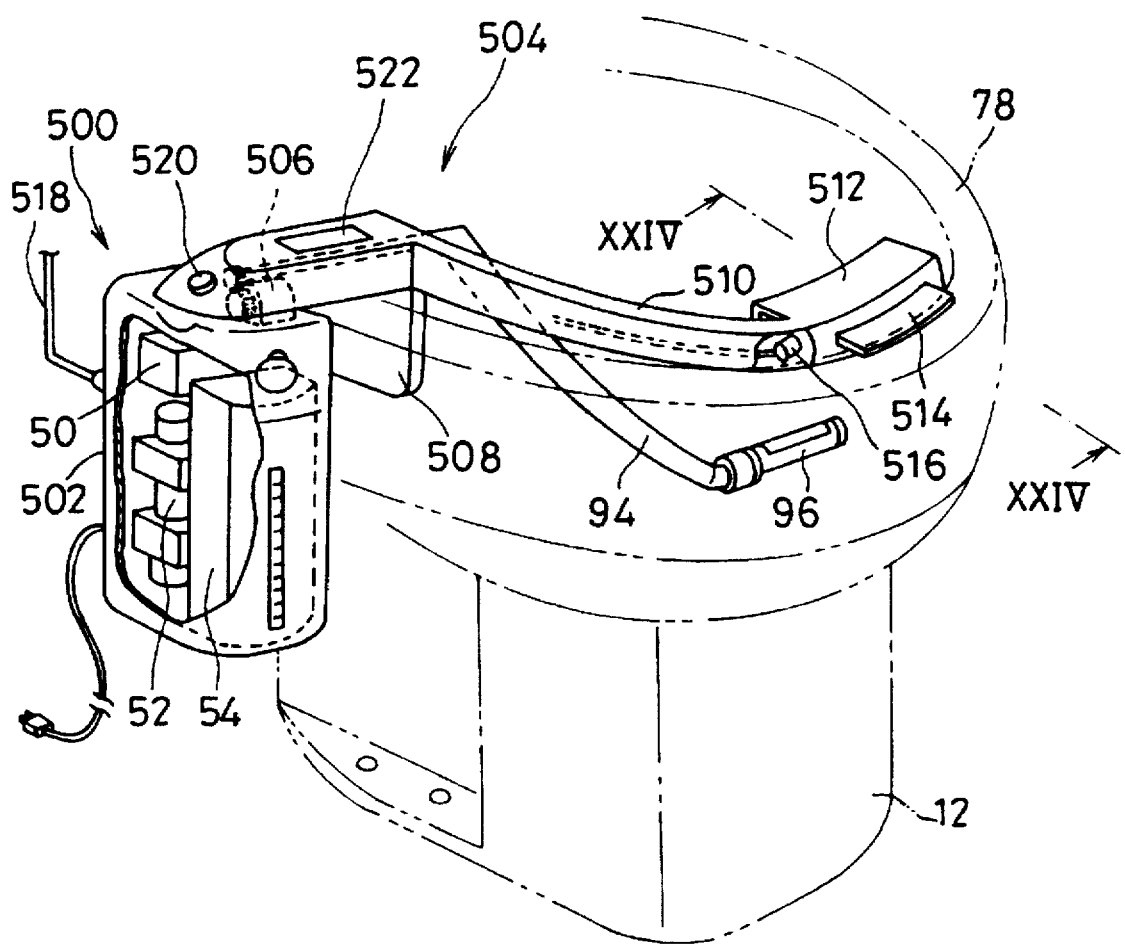
FIG. 23 is a perspective view of a urinalysis unit provided with the third embodiment of the urine sampling apparatus according to the invention.
Figure 24:
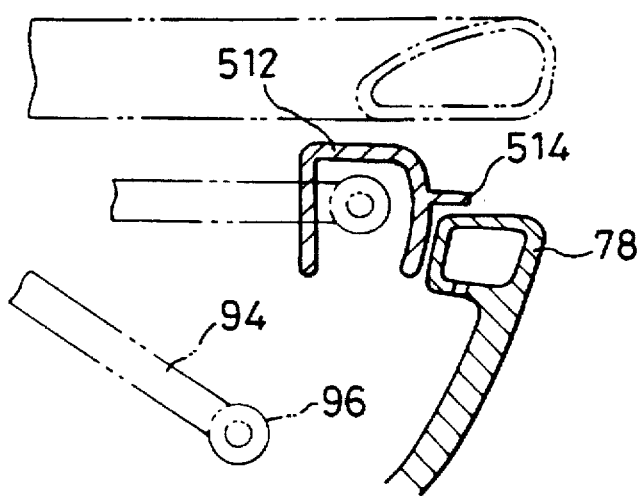
FIG. 24 is a cross-sectional view taken along the line XXIV—XXIV of FIG. 23.

FIGS. 23 and 24 illustrate a urinalysis unit provided with a more simplified third embodiment of the urine sampling apparatus according to the invention. Parts and members identical or similar to those of the first embodiment are designated by like reference numerals. The feature of the third embodiment is that the sampling vessel 96 is moved between the sampling and storage positions only by the rotational movement of the swing arm 94. Accordingly, the electrical drive for the swing arm 94 is simplified.

Referring to FIGS. 23 and 24, the urinalysis unit 500 is designed such that in use it is hooked on the rim 78 of the toilet bowl fixture. The urinalysis unit 500 includes a housing 502 which may be comprised of an upper half and a lower half snap fitted with each other. Received in the housing 502 are a urinalysis device 50 with a polarographic flow cell, an electric syringe pump 52, a carrier liquid reservoir 54, a calibration solution reservoir (not shown) and a control circuit (not shown) which are similar, respectively, to those of the first embodiment.

The swing arm 94 of the urine sampling apparatus 504 is journaled at the upper part of the housing 502 and is adapted to be rotated in the bowl 16 of the toilet fixture 12 by a motor 506 and a gear train. The housing 502 is provided with a vertically extending lug 508 which serves as a hook for hooking the urinalysis unit 500 on the rim 78 of the bowl fixture. The housing 502 is further provided with a support 510 which is curved along the inner contour of the rim 78 and which is provided at the free end with a storage and washing case 512 for storing and washing the sampling vessel 96. The case 512 is provided with a horizontal lug 514 adapted to rest on the rim 78 so that when the urinalysis unit 500 is hooked on the rim 78, the case 512 is located and supported by the rim. A spray nozzle 516 is mounted to the case 512 to wash the sampling vessel 96 placed within the case 512. Water to the nozzle 516 is supplied through a conduit 518 connected to the water line, the water supply being controlled by a solenoid valve, not shown, arranged in the housing 502.

In this embodiment, as a urinalysis start switch 520 provided on the upper part of the housing 502 is depressed, the motor 506 is rotated to bring the swing arm 94 to a sampling position solely by the rotational movement to start urine sampling. Thereafter the urine sample is transferred to the flow cell of the urinalysis device 50 together with the carrier liquid and the results of urinalysis are indicated on a display panel 522 provided on the upper part of the housing 502 in a manner similar to the first embodiment described before. The advantage of this embodiment is that the drive mechanism for the swing arm 94 is simplified and that the urinalysis unit 500 is readily mounted to a standard toilet bowl fixture.

FIGS. 25–31 illustrate the fourth embodiment of the urine sampling apparatus according to the invention. The feature of this embodiment is that the sampling apparatus is mounted to the toilet seat and that the urine sampling vessel is moved only by the rotational movement of the swing arm. In addition, the urine sampling vessel when not in use is adapted to be stored in the vicinity of the inner periphery of the frontal part of the rim of the toilet bowl fixture.

Figure 25:
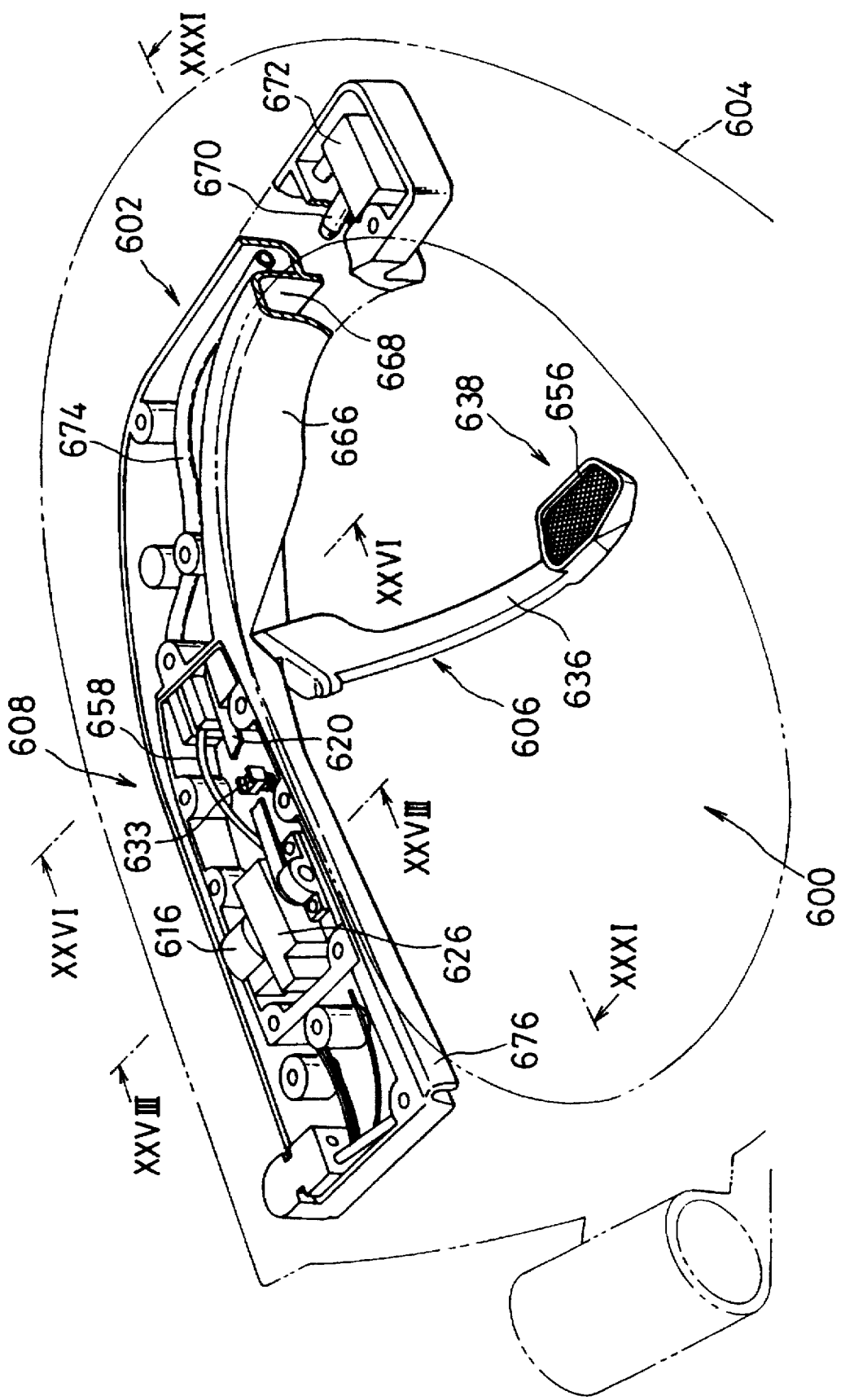
FIG. 25 is a perspective view, partly cut away, showing the fourth embodiment of the urine sampling apparatus according to the invention, with the toilet seat being shown by a phantom line.
Figure 26:
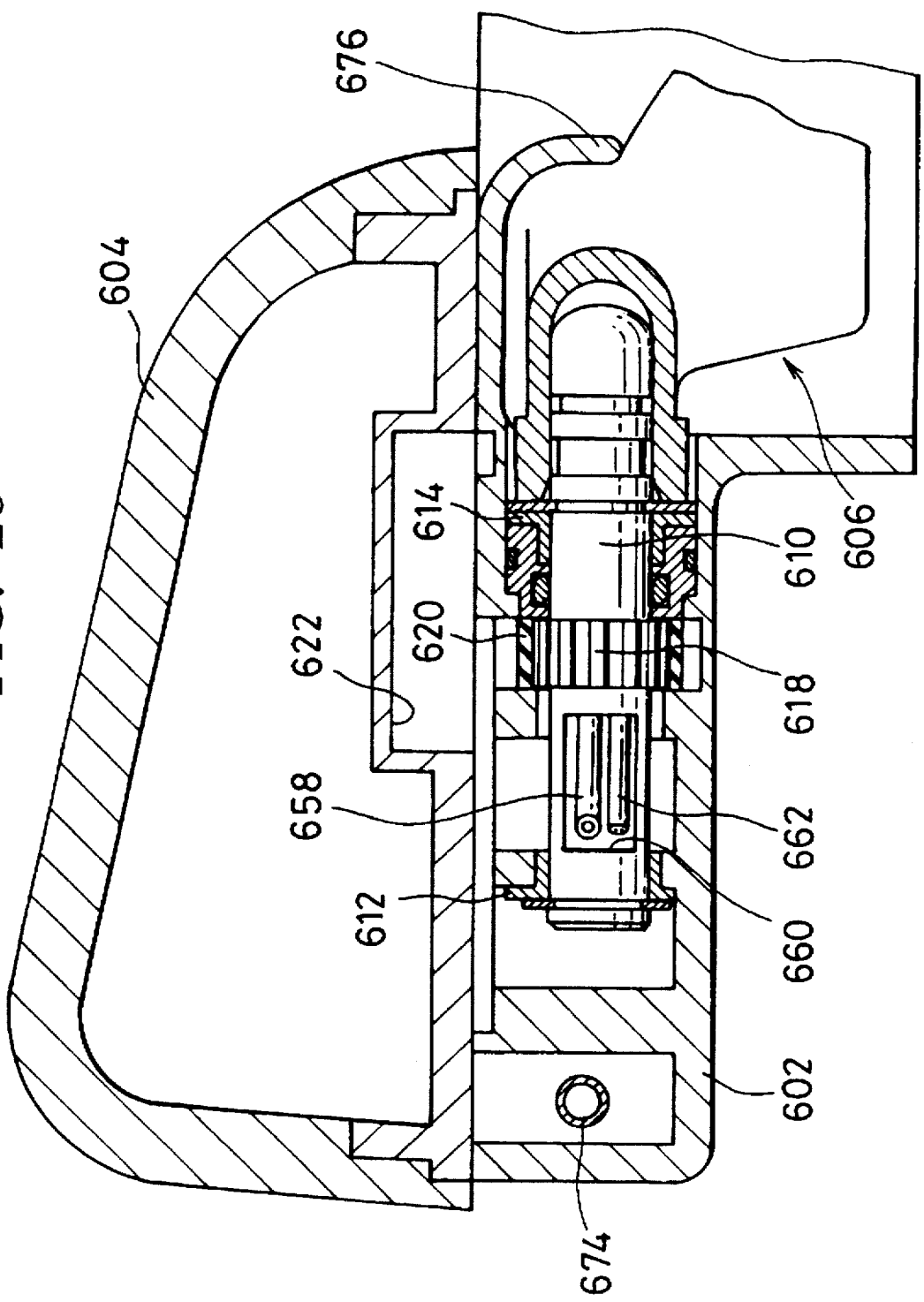
FIG. 26 is an enlarged cross-sectional view taken along the line XXVI—XXVI of FIG. 25.

Referring to FIG. 25, the urine sampling apparatus 600 includes a frame or case 602 which is suitably secured to the underside of the toilet seat 604 by means such as screws. The frame 602 is arcuated along the contour of the toilet seat in such a manner as to be substantially concealed beneath the toilet seat when affixed to the seat. A swing arm 606 is swingably mounted to the frame 602 and is adapted to be moved by a swing arm drive 608. To this end, the swing arm 606 is provided with a spindle 610 which is rotatably supported by the frame 602 by a pair of bearings 612 and 614 as best shown in FIG. 26. The spindle 610 is rotated by a stepping motor 616 via a belt drive. To this end, the spindle 610 is provided with a driven gear 618 which is held in engagement with a cogged belt 620.

Figure 27:
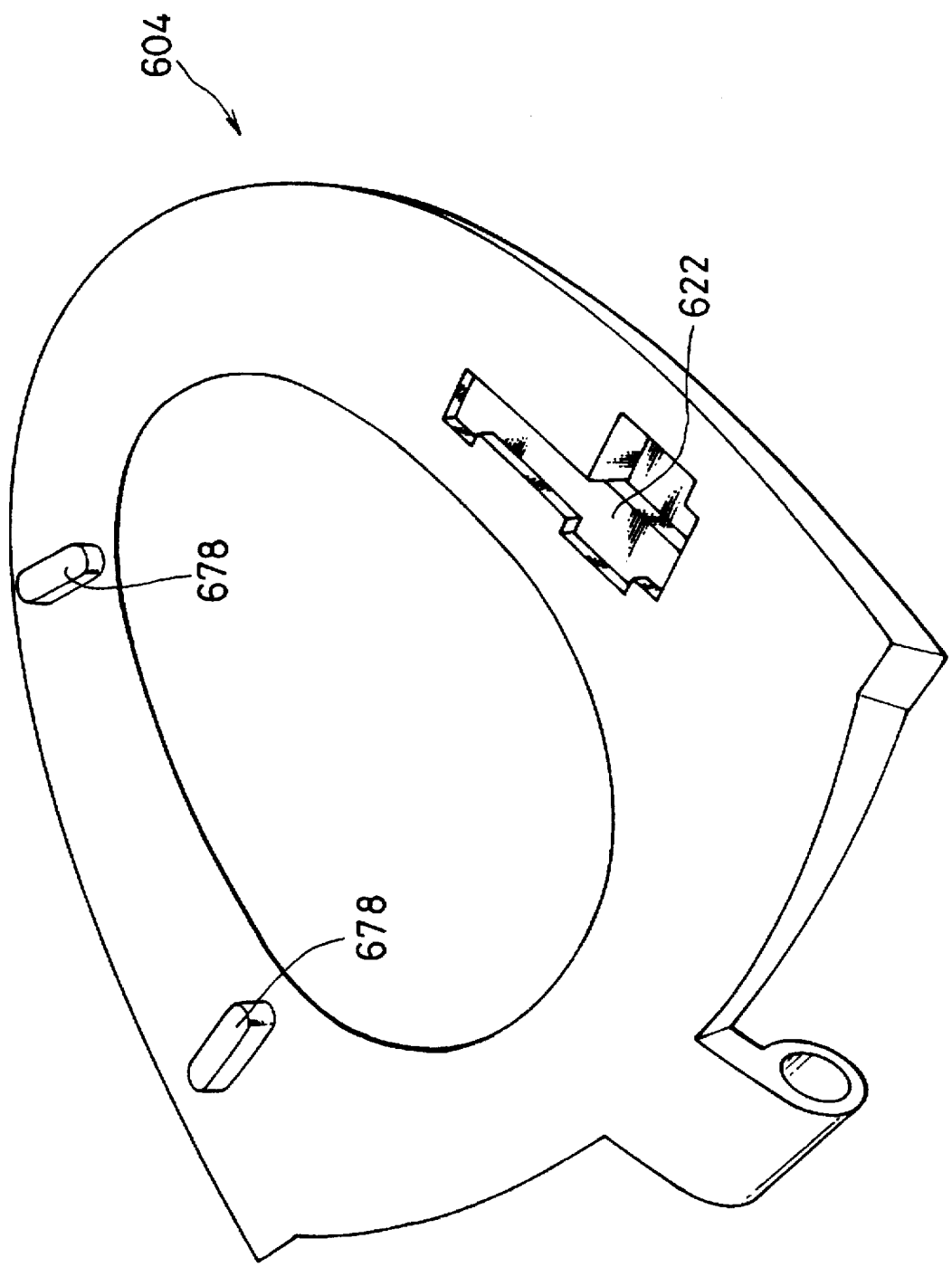
FIG. 27 is a perspective view of the toilet seat of FIG. 25 as reversed.

As will be apparent from FIG. 25, the motor 616 is arranged rearwardly of, and is spaced considerably away from, the spindle 610 of the swing arm 606. As shown in FIG. 27, the toilet seat 604 is provided at the underside thereof with a concavity 622 which is adapted to accommodate the upper parts of the motor 616 and the belt 620. Since the motor 616 is arranged in this manner rearwardly of the frame and the concavity 622 is correspondingly formed in the rear part of the toilet seat 604 in which an increased thickness of the seat is available, it is possible to enlarge the size of the concavity 622 and, hence, to install a larger motor.

Figure 28:
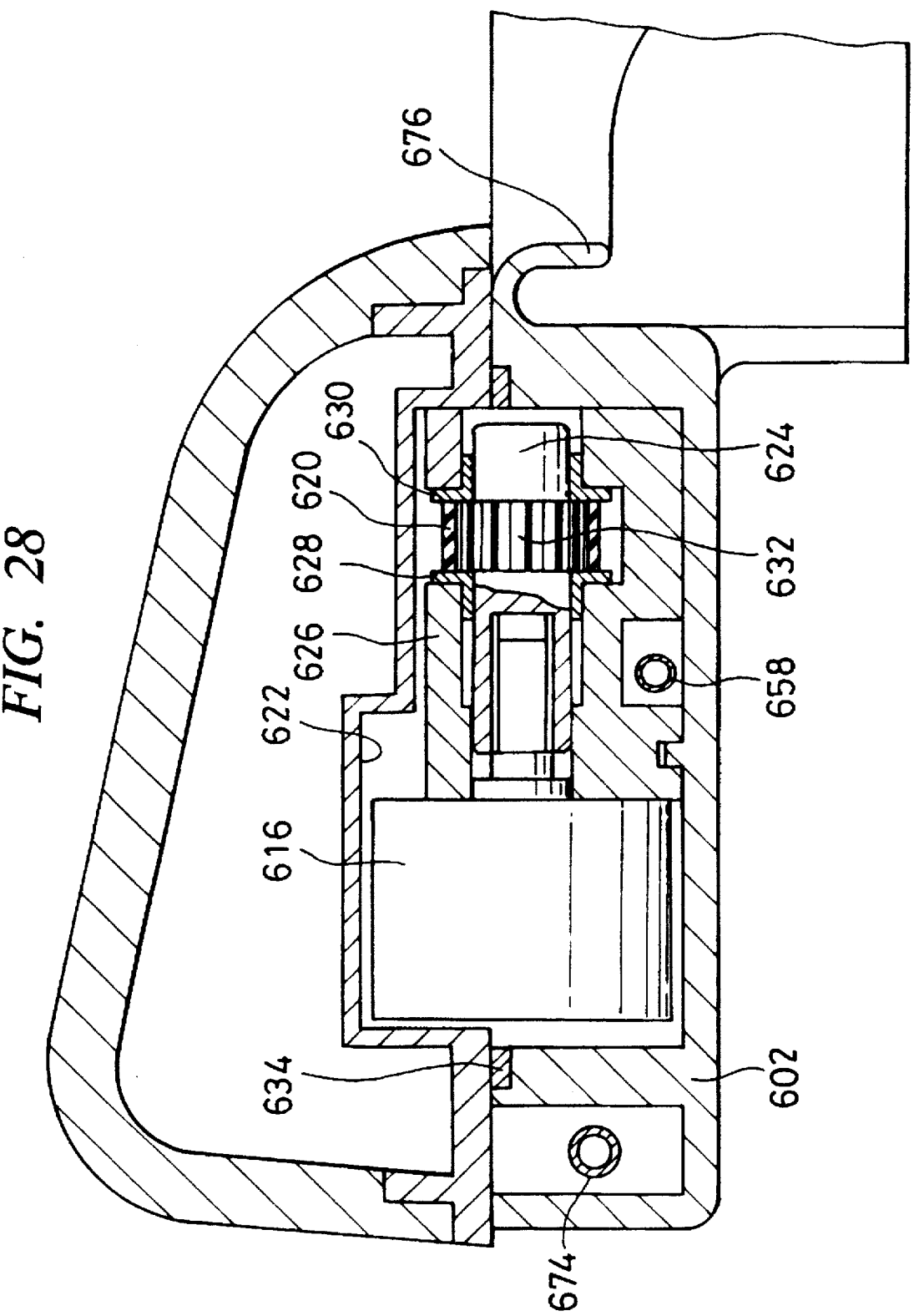
FIG. 28 is an enlarged cross-sectional view taken along the line XXVIII—XXVIII of FIG. 25.

As shown in FIG. 28, an output shaft of the motor 616 is splined to a spindle 624 which is rotatably supported through a pair of bearings 628 and 630 by a bearing block 626 secured to the frame 602. The spindle 626 is provided with a driving gear 632 engaged by the belt 620. As a result, the swing arm 606 will be rotated in response to the rotation of the motor 616. In order to precisely control the angular position of the swing arm, it is desirable to take up any slack in the belt 620. For this reason, an upwardly spring biased slider 633 is arranged on the frame 602 and a conventional tension pulley, not shown for simplicity of drawing, is mounted on the slider in such a manner as to engage the lower run of the belt 620, as shown in FIG. 25. The space which houses the motor 616 and the belt drive is sealed in a waterproof fashion by a packing 634 sandwiched between the frame 602 and the lower surface of the toilet seat.

The swing arm 606 is provided at its lower end 636 with a urine sampling vessel 638. As will be apparent from FIG. 29, the lower end 636 of the swing arm 606 is rearwardly offset in a staggered fashion with respect to the spindle 610 and, hence, with respect to the radius 606A of the swing arm 606, to ensure that the urine sampling vessel 638 is positioned rearwardly as far as possible when the swing arm 606 is rotated to the rearmost extremity position. With this arrangement, it is possible to adapt the sampling vessel to a urine column tending to fall relatively rearwardly of the bowl as in the case of a female user, while using a shortened swing arm.

Figure 30:
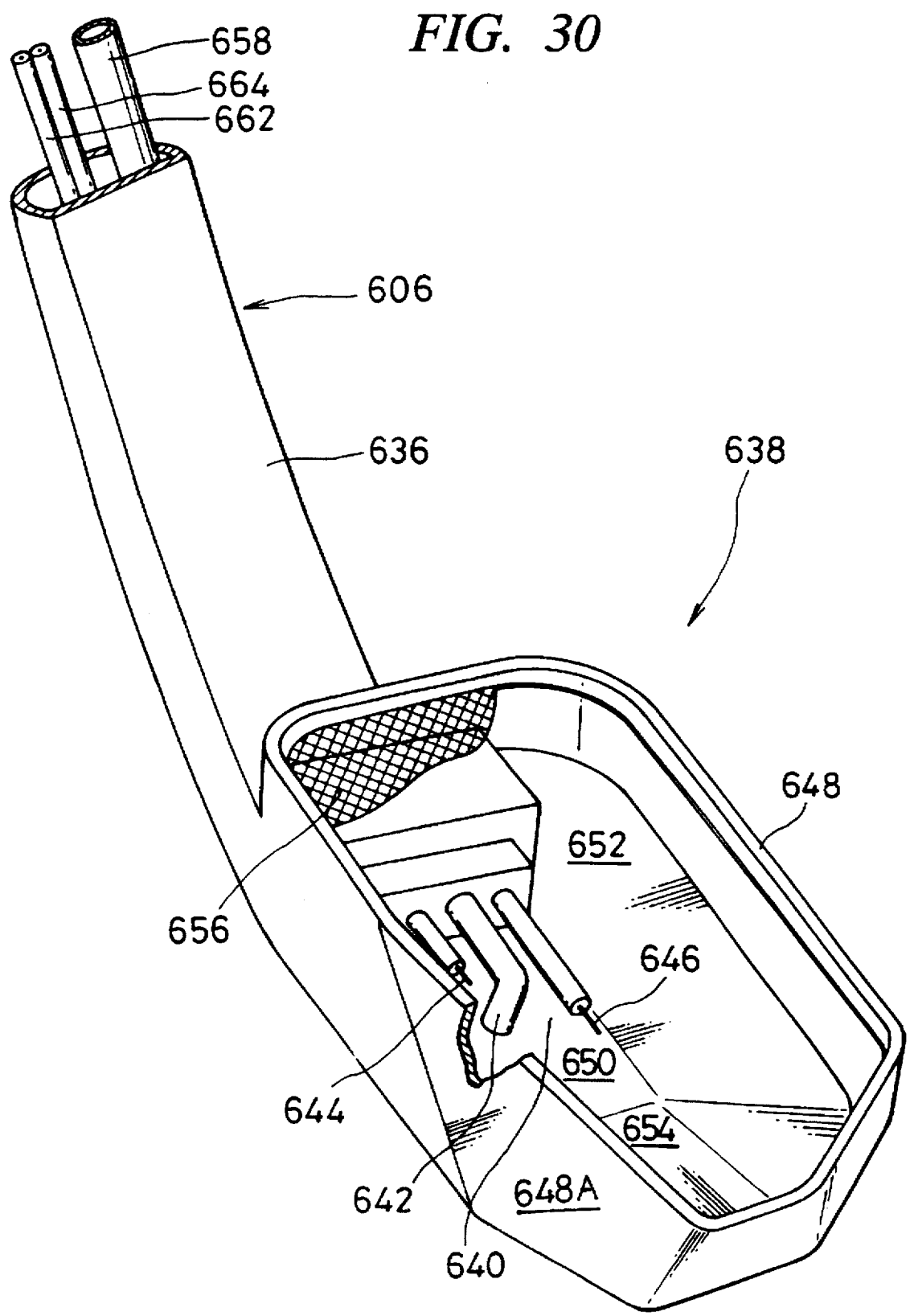
FIG. 30 is an enlarged perspective view, partly cut away, of the sampling vessel shown in FIG. 25; and, FIG. 31 is a cross-sectional view taken along the line XXXI—XXXI of FIG. 25 and showing the swing arm and the urine sampling vessel in various different positions.

As best shown in FIG. 30, the urine sampling vessel 638 has a shallow bilge-like configuration extending transversely of the toilet bowl fixture and is provided at the bottom thereof with a urine pool or sump 640. Similar to the embodiment shown in FIG. 8, an L-shaped suction pipe 642 opens toward the bottom of the urine pool 640 and a pair of sheathed electrodes 644 and 646 project into the urine pool. In order to avoid that these electrodes are inadvertently short-circuited due to the residual droplet of washing water tending to adhere thereto and to therefore avoid erroneous detection of accumulation of urine, these electrodes are exposed only at their free ends with the remainder thereof being sheathed by an insulating material. In addition, one electrode 644 is made longer than the other 646. With this arrangement, the electrodes can be arranged closely with each other since any inadvertent short-circuiting of the electrodes is prevented. As a result, it is possible to reduce the size of the urine pool 640 and to enhance the efficiency of suction through the suction pipe 642.

Figure 29:
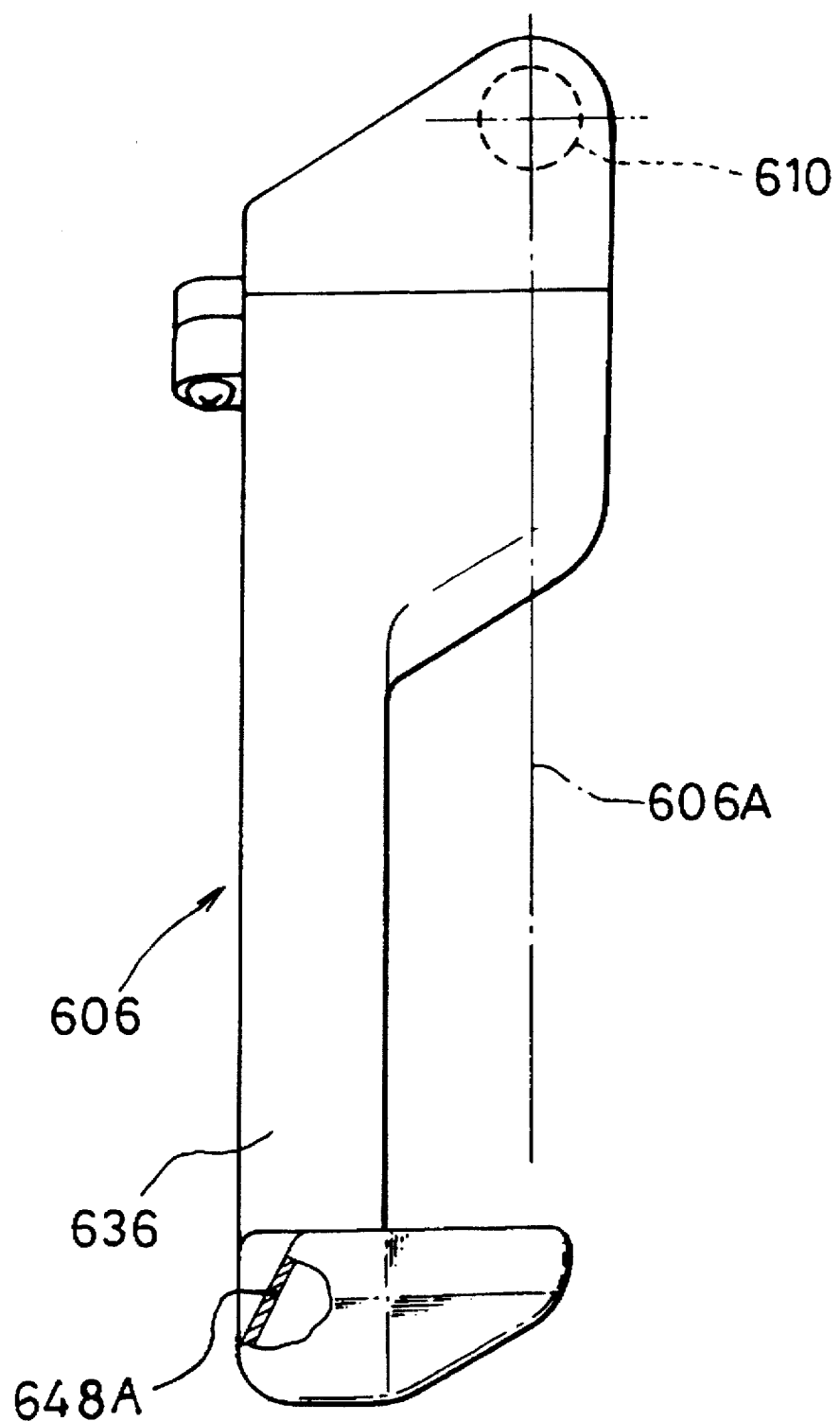
FIG. 29 is a side elevational view of the swing arm shown in FIG. 25, with the sampling vessel being shown partly cut away to show an inclined side wall of the sampling vessel.

In the illustrated embodiment, the urine sampling vessel 638 is comprised of an upright annular side wall 648, a bottom wall 650, a front wall 652 inclined rearwardly toward the bottom wall 650, and a right-hand wall 654 inclined leftwards toward the bottom wall 650, the urine sampling vessel 638 as a whole presenting a generally flat configuration. The rear right-hand portion 648A of the annular side wall 648 is inclined forwardly as shown in FIGS. 29 and 30 for reasons described later.

The inlet opening of the urine sampling vessel 638 is covered by a metallic screen 656 similarly to the embodiment shown in FIGS. 7 and 8 to prevent splash of urine impinging upon the urine sampling vessel 638 as well as to prevent foreign material from entering into the vessel. The L-shaped suction pipe 642 is connected to a flexible tube 658 extending through the inner space of the hollow swing arm 606. The tube 658 is further extended through the inner space of the hollow spindle 610 and is directed rearwardly through a window 660 in the spindle 610 as shown in FIG. 26 for connection to the syringe pump. Similarly, the urine sensing electrodes 644 and 646 are connected, respectively, to lead wires 662 and 664 that extend the inner spaces of the swing arm and the spindle 610. These lead wires are connected to the control circuit of the urinalysis device in a manner described before.

As shown in FIG. 25, the frame 602 of the urine sampling apparatus 600 extends along the contour of the toilet seat up to the frontal part of the toilet seat. As will be apparent from FIGS. 25 and 31, the frame 602 is formed with a channel-shaped wall 666 defining a storage and washing chamber 668 open downwardly toward the toilet bowl. A spray nozzle 670 is directed toward the storage and washing chamber 668 to spray water under pressure toward the urine sampling vessel 638 as returned to the position indicated by the solid line in FIG. 31 so as to cleanse the urine sampling vessel 638 after use. The spray nozzle 670 may be secured to a mounting block 672 fixed to the frame 602 and may be supplied with water under pressure through a water hose 674 connected via a solenoid valve to a water line in a manner similar to the foregoing embodiment. The size of the channel-shaped wall 666 is decreased at the rear part to form a drainage trough 676.

Figure 31:
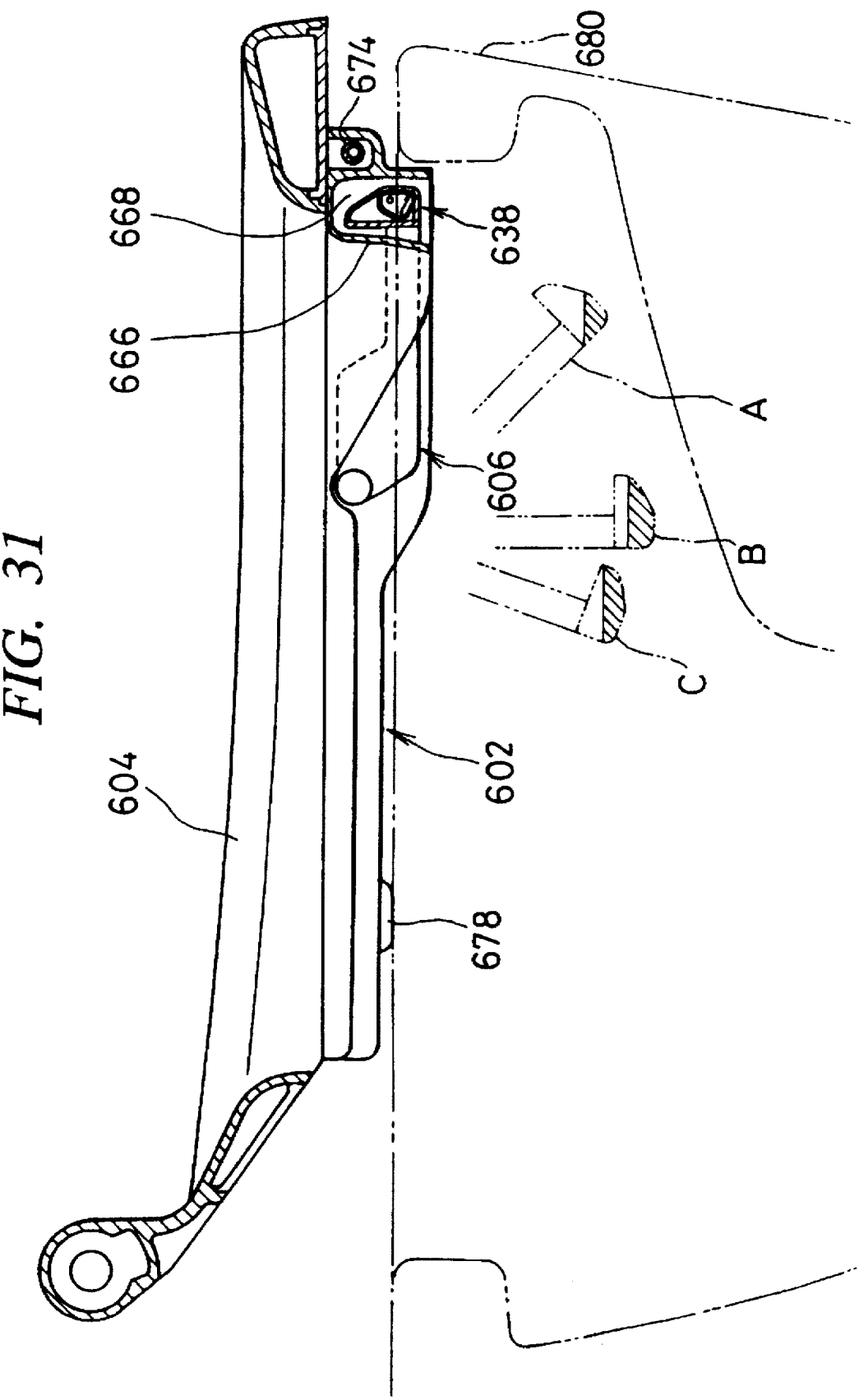

When not in use, the urine sampling vessel 638 is positioned within the storage and washing chamber 668 as shown by the solid line in FIG. 31 so that the toilet seat 604 can be rotated together with the urine sampling vessel 638. Similar to the foregoing embodiment, the toilet seat 604 in its operative position rests upon the rim 680 of the bowl fixture by way of cushioned support legs, two of which are indicated in FIG. 26 by the reference numeral 678, with the other two, not shown, being arranged at the underside of the frame 602.

Since the urine sampling vessel 638 is made substantially flat, it will assume a generally vertical position when stored in the storage and washing chamber 668 as shown by the solid line in FIG. 31, so that the urine sampling vessel 638 can readily be stored in the narrow washing chamber 668. As a result, it is possible to minimize the fore-and-aft dimension of the storage and washing chamber 668 to ensure that the washing chamber 668 is concealed under the toilet seat 604 as far as possible to provide a toilet seat assembly which has a neat appearance.

For sampling of urine released from a male user, the urine sampling vessel 638 may be positioned inclined in the vicinity of the position A shown by the imaginary line in FIG. 31. In this position, the inlet opening of the urine sampling vessel 638 is inclined forwardly so that the urine column ejected forwardly from the user's penis and tending to fall upon the relatively frontal part of the toilet bowl will intersect the inlet opening of the urine sampling vessel 638 generally perpendicularly thereto. Accordingly, the urine sampling vessel 638 receives urine by utilizing the full area of the inlet opening. The shower of urine fallen on the inclined front wall 652 of the sampling vessel will flow toward the rearwardly located urine sump 640 and will accumulate the rein as shown by the hatched area in FIG. 31. Accordingly, urine is drawn from the L-shaped suction pipe 642 without involving air bubble.

In the case of female, urine column tends to fall vertically and rearwardly of the bowl as opposed to male's position. Therefore, when the user is female, the urine sampling vessel 638 may be positioned generally horizontally in the vicinity of the position B shown by the imaginary line. In this position, the inlet opening of the urine sampling vessel 638 will assume a generally horizontal posture so that the inlet opening will be perpendicular to the vertically falling urine column. As a result, urine released from the female user is effectively collected. The inclined frontal and right-hand walls 652 and 654 will act to direct urine impinged on the urine sampling vessel 638 to flow toward the urine pool 640. Collected urine is accumulated in the urine pool as shown by the hatched area in FIG. 31 and is drawn by the suction pipe 642. The sampling vessel 638 may be moved to the extremity position C in accordance with the instructions by the user.

After urine sampling, the urine sampling vessel 638 is returned to the position shown by the solid line in FIG. 31. Similar to the preceding embodiments, the solenoid valve is then opened to cause the spray nozzle 670 to eject washing water. Ejected water forms a spray which washes the outer part of the sampling vessel 638. A part of spray will be rebounded forwardly by the inner surface of the wall 666 of the washing chamber 668 and will penetrate through the now vertically oriented metal screen 656 of the sampling vessel 638 to enter into the inside of the vessel thereby to cleanse the inside of the sampling vessel. Because the rear right-hand portion 648A of the side wall 648 of the sampling vessel is inclined forwardly, washing water as entered into the inside of the vessel will be guided by the wall portion 648A to flow toward the suction pipe 642 and the electrodes 642 and 646 to wash them effectively. Moreover, washing water thus collected toward the suction pipe 642 permits the syringe pump to draw washing water therethrough thereby to wash the inner passages of the suction pipe and the urine transfer tube 658. In order to prevent foreign material from entering the sampling vessel, it is preferable that the mesh of the metal screen 656 is selected to be as small as possible and at least smaller than the inner diameter of the suction pipe 642. However, the smaller the mesh, the more difficult it will be for the spray of washing water to penetrate across the screen. Due to the presence of the inclined side wall portion 648A, however, the limited amount of washing water which has entered inside of the sampling vessel is effectively utilized to wash the interior of the vessel. As the sampling vessel 638 is now in the vertical position, used water is allowed to promptly flow out therefrom and to fall from the downwardly opened storage and washing chamber 668 into the bowl. When the toilet seat is swung up, the residual droplets of cleansing water will be guided by the drainage trough 676 to flow to the rear of the frame and drained into rear part of the bowl 16.

While the present invention has been described herein with reference to the specific embodiments thereof, it is contemplated that the present invention is not limited thereby and various changes and modification may be made the rein. For instance, while the drive 98 for the swing arm 94 has been described as having a rack and pinion mechanism and a lever and cam mechanism driven by a common motor, the rotational movement and the translational movement of the swing arm may be produced by separate motors. While the control system of the urinalysis unit has been described as comprising the control unit installed on the toilet wall and the control circuit arranged in the housing, these parts may be integrated into a single unit.

We claim:

1. A combination comprising: a toilet seat having a substantially sealed hollow structure and suitable to be positioned above a rim of a toilet bowl fixture at a predetermined distance therefrom; a casing mounted to the underside of said toilet seat in such a manner as to be accommodated in a space defined between said rim and said toilet seat; a swing arm provided on an end thereof with a horizontal shaft rotatably supported by said casing and supporting a urine sampling vessel at the other end; and a powered drive mechanism mounted to said casing for driving said swing arm in such a manner that said sampling vessel is moved between a storage position situated underneath the frontal part of said toilet seat and a urine sampling position situated within the inner space of said bowl fixture.

2. A combination according to claim 1, wherein said toilet seat is provided at the underside thereof with a downwardly directed concavity in which said drive mechanism is accommodated in part.

3. An apparatus for sampling urine excreted by an individual seated on a toilet seat at a toilet equipped with a standard water closet bowl fixture, said apparatus comprising:

a frame adapted to be supported by said bowl fixture; an elongated urine sampling vessel having a substantially horizontal axis; a swing arm having one end pivotally supported by said frame and the other end supporting said sampling vessel in such a manner that said axis of said sampling vessel extends substantially perpendicular to the vertical central plane of said bowl fixture; and drive means for driving said swing arm in such a manner that said sampling vessel is moved between a rest position situated adjacent to the frontal part of a rim of said bowl fixture and a urine sampling position situated within the inner space of the bowl.

4. A urine sampling apparatus according to claim 3, wherein said urine sampling vessel is provided with a generally rectangular inlet opening having a longer axis parallel to said horizontal axis, said inlet opening extending substantially perpendicular to the radius of said swing arm to effectively receive urine released into the bowl.

5. A urine sampling apparatus according to claim 4, further comprising a downwardly-open washing chamber disposed inwardly of and adjacent to the inner periphery of the frontal part of the rim of said bowl fixture and cleansing means for ejecting water into said washing chamber, said urine sampling vessel being brought after use in said washing chamber and washed with water, used water being drained into the bowl.

6. A urine sampling apparatus according to claim 5, wherein said urine sampling vessel has a generally flat configuration with a low circumferential side wall and a wide bottom wall to provide a maximum content when said sampling vessel is held in a horizontal position as well as to facilitate storage of said sampling vessel in said washing chamber of a limited fore-and-aft dimension when held in a vertical position.

7. A urine sampling apparatus according to claim 6, wherein said sampling vessel has a urine pool located adjacent the rear part of said side wall and an inclined front wall inclined toward said urine pool to permit urine impinged upon said front wall to flow toward said urine pool.

8. A urine sampling apparatus according to claim 7, wherein said urine pool is situated adjacent the left-hand portion of said side wall, said sampling vessel further having an inclined right-hand wall inclined toward said urine pool to permit urine impinged upon said right-hand wall to flow toward said urine pool.

9. A urine sampling apparatus according to claim 3, wherein said toilet includes a toilet seat pivotally supported by said bowl fixture and wherein, when not in use, said sampling vessel in said rest position is concealed at least in part by the frontal part of said toilet seat.

10. A urine sampling apparatus according to claim 9, wherein said frame is mounted to said toilet seat and wherein said frame extends for a predetermined length along the contour of said toilet seat in such a manner as to be substantially concealed by said toilet seat.

11. A urine sampling apparatus according to claim 10, wherein said frame is mounted to the underside of said toilet seat in a vertical space defined by the rim of said bowl fixture and the toilet seat and wherein said drive means is mounted to said frame.

12. A urine sampling apparatus according to claim 11, wherein said toilet seat is provided with a downwardly open concavity and wherein said drive means is arranged in a space formed by said concavity and the rim of said bowl fixture.

13. A urine sampling apparatus according to claim 12, wherein said toilet seat has a substantially sealed hollow structure.

14. A urine sampling apparatus according to claim 12, wherein said drive means is accommodated at least in part in said downwardly open concavity.

15. A urine sampling apparatus according to claim 3, wherein said frame is secured to a housing mounted on said bowl fixture.

16. A urine sampling apparatus according to claim 3, wherein said frame is detachably mounted to the rim of said bowl fixture.

17. A urine sampling apparatus according to claim 3, wherein said sampling vessel includes a urine pool and urine collecting means inclined toward said urine pool.

18. A urine sampling apparatus according to claim 17, wherein a suction pipe for urine sample opens toward the lower part of said urine pool.

19. A urine sampling apparatus according to claim 18, wherein said swing arm is rotatable between a substantially horizontal position and a substantially vertical position and wherein said suction pipe is arranged at such an angle that an inlet of said suction pipe is directed substantially vertically downwardly when said swing arm is inclined at an angle of about 45°.

20. A urine sampling apparatus according to claim 18, wherein a urine sample transfer conduit in communication with said suction pipe is extended inside of at least part of said swing arm.

21. A urine sampling apparatus according to claim 17, wherein said sampling vessel is detachably mounted to said other end of said swing arm.

22. A urine sampling apparatus according to claim 17, wherein said sampling vessel comprises means for detecting that urine has accumulated in said urine pool to a predetermined level.

23. A urine sampling apparatus according to claim 9, wherein said drive means is operable to move said sampling vessel between said rest position and said urine sampling position only by rotational movement.

24. A urine sampling apparatus according to claim 23, wherein said other end of said swing arm is rearwardly offset in a staggered fashion with respect to the radius of rotation of said swing arm so as to support said sampling vessel rearwardly offset therefrom.

25. A urine sampling apparatus according to claim 23, wherein said drive means includes an electric motor.

26. A urine sampling apparatus according to claim 25, wherein said frame is mounted to the toilet seat and wherein said motor is mounted to said frame rearwardly of said one end of said swing arm, said drive means further comprising a belt drive for transmitting the rotation of said motor to said swing arm.

27. A urine sampling apparatus according to claim 26, wherein said toilet seat is provided with a downwardly open concavity and wherein said motor is received partly in said concavity.

28. A urine sampling apparatus according to claim 3, wherein said drive means comprises a rotational drive mechanism for rotating said swing arm and a translational drive mechanism for translating said swing arm back and forth so as to move said sampling vessel between said rest position and said sampling position by rotational movement as well as by translational movement.

29. A urine sampling apparatus according to claim 28, wherein said drive means is operable to rotate said sampling vessel between a first position substantially concealed by the frontal part of the toilet seat and a second position situated in the bowl space and located rearwardly and downwardly of said first position and is operable to translate said sampling vessel back and forth between said second position and a third position located horizontally rearwardly of said second position.

30. A urine sampling apparatus according to claim 28, wherein said drive means is operable to rotate and translate said sampling vessel between a first position substantially concealed by the frontal part of the toilet seat and a second position situated in the bowl space and located rearwardly and downwardly of said first position and is operable to translate said sampling vessel back and forth between said second position and a third position located horizontally rearwardly of said second position.

31. A urine sampling apparatus according to claim 29 or 30, wherein sampling of urine from a male user is carried out while said sampling vessel is positioned between said first and second positions and sampling of urine from a female user is carried out while said sampling vessel is positioned between said second and third positions.

32. A urine sampling apparatus according to claim 28, wherein said drive means is operable to translate said sampling vessel back and forth between a first position situated above the rim of said bowl fixture and a second position situated horizontally rearwardly of said first position and inwardly of the inner periphery of the rim, to rotate said sampling vessel between said second position and a third position situated in the bowl space and located rearwardly and downwardly of said second position, and to translate said sampling vessel back and forth between said third position and a fourth position located horizontally rearwardly of said third position.

33. A urine sampling apparatus according to claim 28, wherein said drive means is operable to translate said sampling vessel back and forth between a first position situated above the rim of said bowl fixture and a second position situated horizontally rearwardly of said first position and inwardly of the inner periphery of the rim, to rotate and translate said sampling vessel between said second position and a third position situated in the bowl space and located rearwardly and downwardly of said second position, and to translate said sampling vessel back and forth between said third position and a fourth position located horizontally rearwardly of said third position.

34. A urine sampling apparatus according to claim 32 or 33, wherein sampling of urine from a male user is carried out while said sampling vessel is positioned between said second and third positions and sampling of urine from a female user is carried out while said sampling vessel is positioned between said third and fourth positions.

35. A urine sampling apparatus according to claim 28, wherein said translational drive mechanism includes a slider rotatably supporting said one end of said swing arm and guided by said frame for back and forth movement and wherein said rotational drive mechanism includes a motion converting mechanism for converting the back and forth movement of said slider into the rotational movement of said swing arm.

36. A urine sampling apparatus according to claim 35, wherein said translational drive mechanism includes a single motor and a pinion and rack mechanism which are arranged in such a manner that the rotational movement and the translational movement are imparted to said swing arm by said single motor.

37. A urine sampling apparatus according to claim 35, wherein said translational drive mechanism includes a mechanism selected from the group consisting of a pulley and belt mechanism, a lead screw mechanism, a hydraulic cylinder mechanism and a solenoid mechanism.

38. A urine sampling apparatus according to claim 35, wherein said motion converting mechanism includes a lever, with a cam follower, interconnected with said swing arm and a cam with which said cam follower is engaged, said cam having a flat cam surface formed to permit only the translational movement of said swing arm and an inclined cam surface formed to generate a rotational movement of said swing arm in response to the translational movement of said slider.

39. A urine sampling apparatus according to claim 3, wherein said swing arm is arcuated along the inner periphery of said toilet seat.

40. A urine sampling apparatus according to claim 9, further comprising cleansing means, including a spray nozzle, for washing with water said urine sampling vessel as brought to said rest position.

41. A urine sampling apparatus according to claim 40, further comprising a substantially enclosed washing chamber disposed in a space defined between the rim of said bowl fixture and said toilet seat and having a gateway accessible by said sampling vessel, said sampling vessel being washed in said washing chamber after use.

42. A urine sampling apparatus according to claim 41, wherein said spray nozzle is arranged laterally of said sampling vessel in substantially the same horizontal plane as said sampling vessel in said rest position and is directed substantially horizontally toward said sampling vessel to ensure that said sampling vessel is washed in said washing chamber of a limited vertical dimension defined between the rim and the toilet seat.

43. A urine sampling apparatus according to claim 42, wherein a swingable cover is provided at said gateway of said washing chamber, said cover being closed during washing to prevent water from splashing outwardly from said gateway.

44. A urine sampling apparatus according to claim 43, wherein an actuating mechanism is provided to open and close said cover in response to the movement of said sampling vessel, said actuating mechanism being operable to automatically close said cover as said sampling vessel is returned into said washing chamber.

45. A urine sampling apparatus according to claim 41, wherein at least one drainage channel extending from said washing chamber along said toilet seat to the rear part of said toilet seat is provided to discharge used water from said washing chamber into the rear part of the bowl.

46. A urine sampling apparatus according to claim 45, wherein the rear end of said drainage channel is connected to a drain pipe, said drain pipe being arranged to project inwardly of the bowl, as viewed in a plan view, to permit water to fall into the bowl when the toilet seat is swung up.

47. A urine sampling apparatus according to claim 45, wherein said drainage channel is inclined downwardly from the frontal part to the rear part of the toilet seat to permit water in said washing chamber to be discharged even when the toilet seat is held in a horizontal position.

48. A urine sampling apparatus according to claim 40, further comprising a second spray nozzle for washing said swing arm.

49. A urine sampling apparatus according to claim 3, further comprising a downwardly-open storage chamber disposed inwardly of and adjacent to the inner periphery of the frontal part of the rim of said bowl fixture for storing said urine sampling vessel after use, said sampling vessel having a generally flat configuration with a low circumferential side wall and a wide bottom wall to provide a maximum content when said sampling vessel is held in a horizontal position as well as to facilitate storage of said sampling vessel in said storage chamber of a limited fore-and-aft dimension when held in a vertical position.

* * * * *